(12) United States Patent
Yun

(10) Patent No.: US 10,722,587 B2
(45) Date of Patent: Jul. 28, 2020

(54) COMPOSITION FOR INTRACELLULAR DELIVERY CONTAINING ADENOVIRUS PROTEIN VI-DERIVED PEPTIDE AND ANTICANCER PHARMACEUTICAL COMPOSITION CONTAINING SAME

(71) Applicant: INDUSTRY-UNIVERSITY COOPERATION FOUNDATION HANYANG UNIVERSITY, Seoul (KR)

(72) Inventor: Chae Ok Yun, Seoul (KR)

(73) Assignee: GENEMEDICINE CO., LTD. (KR)

( * ) Notice: Subject to any disclaimer, the term of this patent is extended or adjusted under 35 U.S.C. 154(b) by 0 days.

(21) Appl. No.: 15/756,058

(22) PCT Filed: Aug. 31, 2016

(86) PCT No.: PCT/KR2016/009714
§ 371 (c)(1),
(2) Date: Feb. 27, 2018

(87) PCT Pub. No.: WO2017/039311
PCT Pub. Date: Mar. 9, 2017

(65) Prior Publication Data
US 2018/0243430 A1 Aug. 30, 2018

(30) Foreign Application Priority Data

Aug. 31, 2015 (KR) .......................... 10-2015-0122756

(51) Int. Cl.
| | |
|---|---|
| *A61K 47/64* | (2017.01) |
| *A61K 48/00* | (2006.01) |
| *A61P 35/00* | (2006.01) |
| *A61K 39/395* | (2006.01) |
| *A61K 38/10* | (2006.01) |
| *A61K 47/59* | (2017.01) |
| *A61K 35/761* | (2015.01) |

(52) U.S. Cl.
CPC ............ *A61K 47/64* (2017.08); *A61K 35/761* (2013.01); *A61K 38/10* (2013.01); *A61K 39/395* (2013.01); *A61K 47/59* (2017.08); *A61K 48/00* (2013.01); *A61P 35/00* (2018.01); *C12N 2710/10033* (2013.01)

(58) Field of Classification Search
CPC ........ A61K 47/645; A61K 8/64; A61K 38/00; A61K 2800/5426; A61K 38/10; A61K 38/16; A61K 51/088; A61K 47/64; A61K 39/395; A61K 47/59; A61K 35/761; A61K 48/00; A61K 47/50; C07K 2319/10; C07K 14/005; C07K 2319/00; C07K 2319/33; C12N 15/8202; C12N 15/87; C12N 2710/10033; A61P 35/00
See application file for complete search history.

(56) References Cited

U.S. PATENT DOCUMENTS

| | | | | |
|---|---|---|---|---|
| 2004/0249126 | A1* | 12/2004 | Celis | C07K 14/4748 530/350 |
| 2006/0147420 | A1* | 7/2006 | Fueyo | A61K 48/005 424/93.2 |
| 2011/0201112 | A1* | 8/2011 | Rome | C07K 14/005 435/375 |
| 2015/0202324 | A1 | 7/2015 | Hemminki et al. | |
| 2015/0284691 | A1* | 10/2015 | Kummel | A61K 9/1272 424/450 |
| 2017/0080036 | A1* | 3/2017 | Yun | C08G 73/0253 |
| 2017/0119890 | A1* | 5/2017 | Yun | A61K 31/713 |

FOREIGN PATENT DOCUMENTS

| | | |
|---|---|---|
| KR | 20080109751 A * | 12/2008 |
| WO | WO 94/17832 | 8/1994 |

OTHER PUBLICATIONS

Li Y, et. al. pVI [Human mastadenovirus C]. GenBank: ALK80095. 1. Oct. 31, 2015.*
Vaillant R. The role of adenoviral capsid protein VI in cell cycle modulation. Immunology. Université de Bordeaux, 2014. English.*
Kim PH, Kim J, Kim TI, Nam HY, Yockman JW, Kim M, Kim SW, Yun CO. Bioreducible polymer-conjugated oncolytic adenovirus for hepatoma-specific therapy via systemic administration. Biomaterials. Dec. 2011;32(35):9328-42. Epub Sep. 16, 2011.*
Guo Z, Peng H, Kang J, Sun D. Cell-penetrating peptides: Possible transduction mechanisms and therapeutic applications. Biomed Rep. May 2016;4(5):528-534. Epub Mar. 23, 2016.*
Liu S, Mao Q, Zhang W, Zheng X, Bian Y, Wang D, Li H, Chai L, Zhao J, Xia H. Genetically modified adenoviral vector with the protein transduction domain of Tat improves gene transfer to CAR-deficient cells. Biosci Rep. Apr. 2009;29(2):103-9.*
"Understanding Melanoma: About Melanoma—Types of Melanoma." AIM at Melanoma Foundation, 2014. https://www.aimatmelanoma.org/about-melanoma/types-of-melanoma/.*
Carlisle et al., "Adenovirus Hexon Protein Enhances Nuclear Delivery and Increases Transgene Expression of Polyethylenimine/Plasmid DNA Vectors", Molecular Therapy, vol. 4, No. 5, Nov. 2001, pp. 473-483.
International Search Report for PCT/KR2016/009714, dated Nov. 18, 2016, 8 pages.
Jung et al., "Safety Profiles and Antitumor Efficacy of Oncolytic Adenovirus Coated with Bioreducible Polymer in the Treatment of a CAR Negative Tumor Model", Biomacromolecules 2015, 16, pp. 87-96.

(Continued)

*Primary Examiner* — Rachel B Gill
(74) *Attorney, Agent, or Firm* — Adsero IP

(57) ABSTRACT

The present invention relates to a composition for intracellular delivery containing an adenovirus protein VI-derived peptide and an anti-cancer pharmaceutical composition containing the same. According to the present invention, the use of the peptide or peptide-polymer composite of the present invention improves intracellular delivery efficiency of a nucleic acid, a peptide, a poly-peptide, an antibody, a chemical material, or a virus. Therefore, the peptide or peptide-polymer composite of the present invention can be favorably used as an intracellular delivery system for various therapeutics.

9 Claims, 20 Drawing Sheets

Specification includes a Sequence Listing.

(56) References Cited

OTHER PUBLICATIONS

Medina-Kauwe, "Development of adenovirus capsid proteins for targeted therapeutic delivery", Ther Deliv., Feb. 4, 2013(2):267-277.

Nicklin et al., "The Influence of Adenovirus Fiber Structure and Function on Vector Development for Gene Therapy", Molecular Therapy, vol. 12, No. 3, Sep. 2005, pp. 384-393.

Vigant et al., "Substitution of Hexon Hypervariable Region 5 of Adenovirus Serotype 5 Abrogates Blood Factor Binding and Limits Gene Transfer to Liver", Molecular Therapy, vol. 16, No. 8, pp. 1474-1480, Aug. 2008.

European Search Report for application 16842277.2, dated Aug. 7, 2018, 10 pages.

Murayama et al., "Effect of Amino Acid Substitution in the Hydrophobic Face of Amphiphilic Peptides on Membrane Curvature and Perturbation: N-Terminal Helix Derived From Adenovirus Internal Protein VI As a Model", PeptideScience, vol. 106, No. 4:430-439.

Wiethoff et al., "Adenovirus Protein VI Mediates Membrane Disruption following Capsid Disassembly", Journal of Virology, Feb. 2005, p. 1992-2000, vol. 79, No. 4, pp. 1992-2000. (Downloaded from http://jvi.asm.org/ on Jul. 23, 2018).

Alhakamy et al., "Noncovalently associated cell-penetrating peptides for gene delivery applications", Ther. Deliv. (2013) 4(6), 741-757.

Li et al., "Intracellular Delivery of Molecular Cargo Using Cell-Penetrating Peptides and the Combination Strategies", Int. J. Mol. Sci. 2015, 16, 19518-19536.

Office Action for European Application No. 16842277.2, dated Apr. 3, 2020, 10 pages.

* cited by examiner

FIG. 7

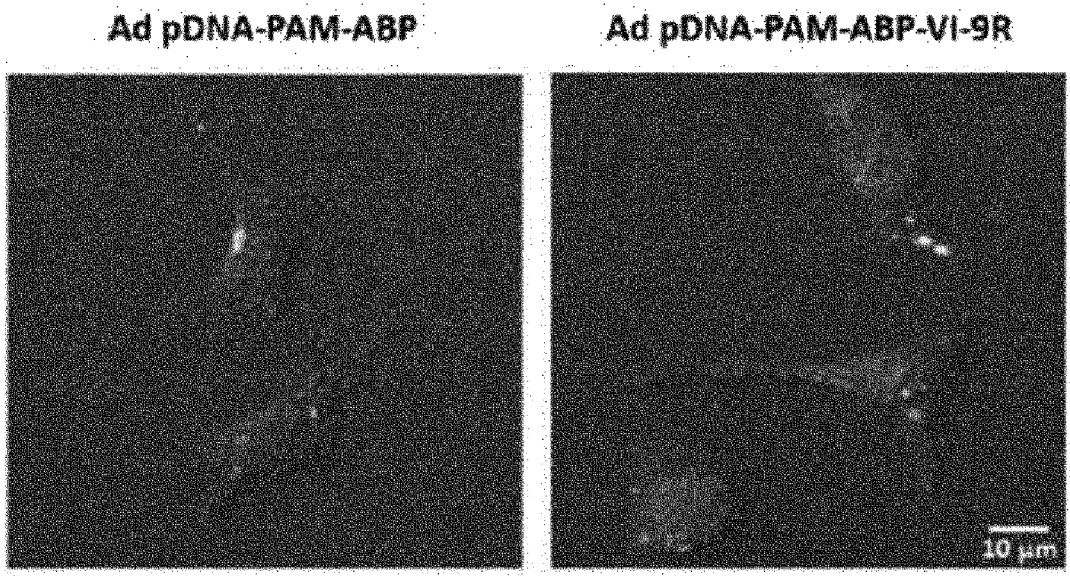

FIG. 8

- Hydrophobic amino acid
- Positive charged amino acid
- Amphiphilic amino acid
- Others

| Name of Peptide | Sequnce | Number of Sequnce |
|---|---|---|
| VI | SWGSLWSGKNFG | 13 |
| VI-9R | SWGSLWSGKNFGRRRRRRRRR | 22 |
| mVI | AFSWGSLWSGKNFG | 15 |
| mVI-TAT | AFSWGSLWSGKNFGRKKRRQRRR | 24 |
| mVI-TAT-A | AFSWGSLWSGKNFGRKKRRQRRRALAE | 28 |
| mVI-G-TAT-A | AFSWGSLWSGKNFGFLGRKKRRQRRRALAE | 31 |
| mVI-A-TAT | AFSWGSLWSGKNFGALAERKKRRQRRR | 28 |
| mVI-G-A-TAT | AFSWGSLWSGKNFGFLGALAERKKRRQRRR | 31 |
| TAT | YGRKKRRQRRR | 11 |
| NLS | PKKKRKVPKKKRKV | 14 |

SEQUENCE LISTING

```
<160> NUMBER OF SEQ ID NOS: 11

<210> SEQ ID NO 1
<211> LENGTH: 13
<212> TYPE: PRT
<213> ORGANISM: VI

<400> SEQUENCE: 1

Ser Trp Gly Ser Leu Trp Ser Gly Ile Lys Asn Phe Gly
1               5                   10

<210> SEQ ID NO 2
<211> LENGTH: 22
<212> TYPE: PRT
<213> ORGANISM: Artificial sequence
<220> FEATURE:
<223> OTHER INFORMATION: VI-9R

<400> SEQUENCE: 2

Ser Trp Gly Ser Leu Trp Ser Gly Ile Lys Asn Phe Gly Arg Arg Arg
1               5                   10                  15

Arg Arg Arg Arg Arg Arg
            20

<210> SEQ ID NO 3
<211> LENGTH: 15
<212> TYPE: PRT
```

```
<213> ORGANISM: Artificial sequence
<220> FEATURE:
<223> OTHER INFORMATION: mVI

<400> SEQUENCE: 3

Ala Phe Ser Trp Gly Ser Leu Trp Ser Gly Ile Lys Asn Phe Gly
1               5                   10                  15

<210> SEQ ID NO 4
<211> LENGTH: 24
<212> TYPE: PRT
<213> ORGANISM: Artificial sequence
<220> FEATURE:
<223> OTHER INFORMATION: mVI-TAT

<400> SEQUENCE: 4

Ala Phe Ser Trp Gly Ser Leu Trp Ser Gly Ile Lys Asn Phe Gly Arg
1               5                   10                  15

Lys Lys Arg Arg Gln Arg Arg Arg
            20

<210> SEQ ID NO 5
<211> LENGTH: 28
<212> TYPE: PRT
<213> ORGANISM: Artificial sequence
<220> FEATURE:
<223> OTHER INFORMATION: mVI-TAT-A

<400> SEQUENCE: 5

Ala Phe Ser Trp Gly Ser Leu Trp Ser Gly Ile Lys Asn Phe Gly Arg
1               5                   10                  15

Lys Lys Arg Arg Gln Arg Arg Arg Ala Leu Ala Glu
            20                  25

<210> SEQ ID NO 6
<211> LENGTH: 31
<212> TYPE: PRT
<213> ORGANISM: Artificial sequence
<220> FEATURE:
<223> OTHER INFORMATION: mVI-G-TAT-A

<400> SEQUENCE: 6

Ala Phe Ser Trp Gly Ser Leu Trp Ser Gly Ile Lys Asn Phe Gly Phe
1               5                   10                  15

Leu Gly Arg Lys Lys Arg Arg Gln Arg Arg Arg Ala Leu Ala Glu
            20                  25                  30

<210> SEQ ID NO 7
<211> LENGTH: 28
<212> TYPE: PRT
<213> ORGANISM: Artificial sequence
<220> FEATURE:
<223> OTHER INFORMATION: mVI-A-TAT

<400> SEQUENCE: 7

Ala Phe Ser Trp Gly Ser Leu Trp Ser Gly Ile Lys Asn Phe Gly Ala
1               5                   10                  15

Leu Ala Glu Arg Lys Lys Arg Arg Gln Arg Arg Arg
            20                  25

<210> SEQ ID NO 8
<211> LENGTH: 31
<212> TYPE: PRT
<213> ORGANISM: Artificial sequence
<220> FEATURE:
```

```
<223> OTHER INFORMATION: mVI-G-A-TAT

<400> SEQUENCE: 8

Ala Phe Ser Trp Gly Ser Leu Trp Ser Gly Ile Lys Asn Phe Gly Phe
1               5                   10                  15

Leu Gly Ala Leu Ala Glu Arg Lys Lys Arg Arg Gln Arg Arg Arg
            20                  25                  30

<210> SEQ ID NO 9
<211> LENGTH: 11
<212> TYPE: PRT
<213> ORGANISM: Artificial sequence
<220> FEATURE:
<223> OTHER INFORMATION: TAT

<400> SEQUENCE: 9

Tyr Gly Arg Lys Lys Arg Arg Gln Arg Arg
1               5                   10

<210> SEQ ID NO 10
<211> LENGTH: 14
<212> TYPE: PRT
<213> ORGANISM: Artificial sequence
<220> FEATURE:
<223> OTHER INFORMATION: NLS

<400> SEQUENCE: 10

Pro Lys Lys Lys Arg Lys Val Pro Lys Lys Lys Arg Lys Val
1               5                   10

<210> SEQ ID NO 11
<211> LENGTH: 62
<212> TYPE: PRT
<213> ORGANISM: Artificial sequence
<220> FEATURE:
<223> OTHER INFORMATION: mVI-G-A-TAT dimer

<400> SEQUENCE: 11

Ala Phe Ser Trp Gly Ser Leu Trp Ser Gly Ile Lys Asn Phe Gly Phe
1               5                   10                  15

Leu Gly Ala Leu Ala Glu Arg Lys Lys Arg Arg Gln Arg Arg Arg Ala
            20                  25                  30

Phe Ser Trp Gly Ser Leu Trp Ser Gly Ile Lys Asn Phe Gly Phe Leu
        35                  40                  45

Gly Ala Leu Ala Glu Arg Lys Lys Arg Arg Gln Arg Arg Arg
    50                  55                  60
```

COMPOSITION FOR INTRACELLULAR DELIVERY CONTAINING ADENOVIRUS PROTEIN VI-DERIVED PEPTIDE AND ANTICANCER PHARMACEUTICAL COMPOSITION CONTAINING SAME

CROSS-REFERENCE TO RELATED APPLICATION

This application claims priority to and is a 35 U.S.C. § 371 national phase application of PCT/KR2016/9714 (WO2017/039311), filed on Aug. 31, 2016 entitled "COMPOSITION FOR INTRACELLULAR DELIVERY CONTAINING ADENOVIRUS PROTEIN VI-DERIVED PEPTIDE AND ANTICANCER PHARMACEUTICAL COMPOSITION CONTAINING SAME", which application claims priority to and the benefit of Korean Patent Application No. 10-2015-0122756, filed Aug. 31, 2015; the disclosures of which are incorporated herein by reference in their entirety.

SEQUENCE STATEMENT

Incorporated by reference herein in its entirety is the Sequence Listing entitled "G18U10C0031PUS_ST25," created Feb. 22, 2018, size of 4 kilobyte.

TECHNICAL FIELD

The present invention relates to a composition for intracellular delivery containing adenovirus protein VI-derived peptide and anticancer pharmaceutical composition containing the same.

BACKGROUND ART

Since most conventional gene therapeutics for cancer are injected into a body through local administration, there is a limit of decreasing accessibility with respect to metastatic cancer spreading all over the body. Therefore, in the cases of diseases imperceptibly spreading all over the body, for example, metastatic cancer, although such diseases have been generally excluded from gene therapies until now, it is necessary to develop products capable of systemic administration to expand the gene therapy market.

As adenoviruses have become popular as gene transfer vectors due to various advantages, they are being increasingly used for cancer gene therapy, and used most frequently in patient clinical trials. Particularly, oncolytic adenoviruses capable of killing only cancer cells by being selectively proliferated only in the cancer cells can not only exhibit a therapeutic effect in primary infected cells, but also considerably increase a cancer therapeutic effect since the therapeutic effect can keep spreading like a domino effect due to a series of infections of surrounding tumor cells by a proliferating virus and killing of cancer cells. Meanwhile, when a therapeutic gene is loaded in an oncolytic adenovirus, a therapeutic gene is limitedly expressed only in cancer cells with high efficiency, and thus the therapeutic effect can be synergistically improved. In addition, since the proliferation of oncolytic adenoviruses in peripheral normal cells is inhibited, killing of cells does not occur, and thus safety is high. For this reason, the therapeutic gene-loaded adenoviruses have attracted attention as the next generation anti-cancer therapeutics.

However, in systemic administration, the virus-based gene therapeutics have limitations of fast removal of viruses caused by immune cells in the blood, a very small amount of the therapeutics delivered to target tumor tissue, and hepatotoxicity caused by accumulating a large amount of the therapeutics. In addition, in repeated administration, since a high concentration of neutralizing antibodies is formed, a therapeutic effect caused by the repeated administration is considerably reduced. Because of these reasons, all currently-developed oncolytic adenoviruses used in cancer treatment are locally administered. Therefore, it is necessary to develop novel and innovative methods that allow systemic administration and effectively deliver adenoviruses to a target such as tumor cells.

As one of the novel methods, a method for treating cancer by delivering the DNA of an oncolytic adenovirus to target tumor cells, instead of using the oncolytic adenovirus itself as a therapeutic, has been suggested. To this end, it is necessary to develop a method for more safely and efficiently delivering adenovirus DNA to tumor cells in the human body.

Throughout this specification, numerous papers and patent documents are provided as references and cited references thereof are shown. The disclosure of the cited papers and patent literatures are incorporated herein by reference in their entirety, and thus the level of the technological field including the present application and the scope of the present application are more fully described.

DISCLOSURE

Technical Problem

The inventors have tried to develop a composition or method that can exhibit an oncolytic effect by more efficiently delivering viral DNA or viruses into tumor cells. As a result, the inventors identified that, when viral DNA or viruses were delivered into tumor cells using an adenovirus virus VI-derived peptide or a composite of the peptide and a polymer, intracellular introduction efficiency of the viral DNA or viruses is improved, and an excellent anticancer therapeutic effect is exhibited, and thus completed the present invention.

Therefore, the present invention is directed to providing a composition containing a peptide of SEQ ID NO: 1, a modified peptide of SEQ ID NO: 1 or a dimer thereof for efficiently delivering a bioactive substance into cells.

The present invention is also directed to providing a use of a peptide of SEQ ID NO: 1, a modified peptide of SEQ ID NO: 1 or a dimer thereof for intracellular delivery of a bioactive substance.

The present invention is also directed to providing a delivery method using a peptide of SEQ ID NO: 1, a modified peptide of SEQ ID NO: 1 or a dimer thereof for intracellular delivery of a bioactive substance.

The present invention is also directed to providing a pharmaceutical composition including the composition and viral DNA or viruses for treating cancer, a use thereof for treating cancer, and a method for treating cancer, which includes administering the composition to a subject.

Other objects and advantages of the present invention will be more clearly explained with reference to detailed description, claims and drawings of the present invention as follows.

Technical Solution

In one aspect of the present invention, the present invention provides a composition containing a peptide of SEQ ID NO: 1, a modified peptide of SEQ ID NO: 1 or a dimer thereof for efficiently delivering a bioactive substance into cells, wherein the bioactive substance may be any one selected from the group consisting of a nucleic acid, a peptide, a polypeptide, an antibody, a chemotherapeutic and a virus:

SEQ ID NO: 1: SWGSLWSGIKNFG

In another aspect of the present invention, the present invention provides a composition for intracellular delivery, which includes a peptide to which a positively-charged amino acid is additionally linked to the N- or C-terminus of the peptide of SEQ ID NO: 1.

According to an exemplary embodiment of the present invention, the positively-charged amino acid is arginine (Arg) or lysine (Lys).

In still another aspect of the present invention, the present invention provides a composition for intracellular delivery, which includes a peptide to which a hydrophobic amino acid is additionally linked to the N- or C-terminus of the peptide of SEQ ID NO: 1.

According to an exemplary embodiment of the present invention, the hydrophobic amino acid is alanine (Ala) or phenylalanine (Phe), and more specifically, alanine-phenylalanine may be linked to the N-terminus of the peptide of SEQ ID NO: 1.

In yet another aspect of the present invention, the present invention provides a composition for intracellular delivery of a bioactive substance, which includes the peptide of SEQ ID NO: 1 or a dimer of the modified peptide of SEQ ID NO: 1.

In yet another aspect of the present invention, the present invention provides a composition for intracellular delivery of a bioactive substance, which includes the peptide of SEQ ID NO: 1, the modified peptide of SEQ ID NO: 1 or a dimer thereof, and a biocompatible polymer.

According to an exemplary embodiment of the present invention, the biocompatible polymer is a polymer including (i) an escapable portion from immune reactions, (ii) a chargeable portion and (iii) a bioreducible portion having a disulfide bond.

According to an exemplary embodiment of the present invention, the escapable portion from immune reactions is any one selected from polyethylene glycol (PEG), polyalkylene oxide [e.g., polyoxyethylene, polyoxypropylene or a copolymer thereof (for example, a polyethyleneoxide-polypropyleneoxide-polyethylene oxide copolymer)], a polyphenylene oxide-PEG-polyalkylene oxide copolymer, poly(methoxyethyl methacrylate), poly(methacryloyl phosphatidylcholine), perfluorinated polyether, dextran and polyvinylpyrrolidone.

In yet another aspect of the present invention, the present invention provides a pharmaceutical composition for treating cancer, which includes (a) (i) any one or more materials selected from the group consisting of a peptide of SEQ ID NO: 1 or a modified peptide thereof, the peptide or a dimer thereof, and a biocompatible polymer, liposome, niosome and a nanomaterial, (ii) a therapeutically effective amount of a composite including viral DNA or viruses; and (b) a pharmaceutically acceptable carrier.

Examples of biocompatible polymers used in the present invention are as follows, but the present invention is not limited thereto:

i. Polymer

Examples of polymer-based carriers, which are widely used as a non-virus vector, include gelatin, chitosan (Carreno G B, Duncan R. Evaluation of the biological properties of soluble chitosan and chitosan microspheres. Int J Pharm 148:231-240 (1997)) poly-L-lysine (PLL; Maruyama A, Ishihara T, Kim J S, Kim S W, Akaike T. Nanoparticle DNA carrier with poly (L-lysine) grafted polysaccharide copolymer and poly(D, L-lactide). Bioconjugate Chem 8:735-742 (1997)) and polyethyleneamine (PEI; Abdallah B, Hassan A, Benoist C, Goula D, Behr J P, Demeneix B A. A powerful non-virus vector for in vivo gene transfer into the adult mammalian brain: Polyethyleneimine. Human Gene Ther 7:1947-1954 (1996)). The polymer-based vectors have the following advantages: low incidence rates of immune responses and acute toxicity, simple preparation methods and facilitation of mass-production.

ii. Liposomes and Niosomes

Liposomes are automatically formed by phospholipids dispersed in an aqueous phase. Examples of successfully delivering foreign DNA molecules into cells using liposomes are disclosed in Nicolau and Sene, Biochim. Biophys. Acta, 721:185-190 (1982) and Nicolau et al., Methods Enzymol., 149:157-176 (1987). Meanwhile, a reagent that is most widely used in transformation of animal cells using liposomes is lipofectamine (Gibco BRL). A liposome containing a target nucleotide sequence to be delivered delivers the target nucleotide sequence to be delivered into cells by interacting with the cells through a mechanism such as endocytosis, adsorption onto a cell surface or fusion with a plasma cell membrane.

On the other hand, while a liposome is made from a phospholipid, a niosome is a bilayer transporter consisting of combination of a non-ionic surfactant and cholesterol, encloses polar and non-polar materials, and is osmotically active and stable, compared to a liposome which is a lipid particle carrier via a phospholipid. In addition, there are no specific conditions in storage and handling of a surfactant used in preparation.

iii. Nanoparticles

The term "nanoparticle" used herein refers to a biocompatible polymeric material having a size of several to hundreds of nanometers, and may be, for example, polyetheleneglycol (PEG), poly-lactide (PLA), polyglycolide (PGA), poly-lactide-co-glycolide (PLGA), poly-ε-carprolactone (PCL), hyaluronic acid (HA), chitosan, or serum albumin.

Since the pharmaceutical composition includes the above-described peptide or peptide-polymer composite as an active ingredient, common content will be omitted to avoid excessive complexity in the specification.

The "viral DNA" used herein includes whole, partially-deleted or partially-modified viral genomic DNA.

According to an exemplary embodiment of the present invention, when the viral DNA is adenovirus DNA (Ad pDNA-polymer-dimeric peptide composite), the weight ratio of the Ad pDNA:polymer may be 1:1 to 1:1000, and the weight ratio of the Ad pDNA:dimer peptide may be 1:0.001 to 1:1000, but the present invention is not limited thereto.

The viruses used in the present invention include a certain virus, and specifically, a virus used as a gene therapeutic. For example, the viruses are as follows, but the present invention is not limited thereto.

i. Adenoviruses

Adenoviruses have been widely used as a gene transfer vector due to a medium-sized genome, convenient manipulation, a high titer, a wide range of target cells and excellent infectivity. Both termini of the genome include 100 to 200 bp of an inverted terminal repeat (ITR), which is a cis-element essential for DNA replication and packaging. E1 regions (E1A and E1B) of the genome encode transcriptional proteins and proteins that regulate the transcription of genes of a host cell. E2 regions (E2A and E2B) encode proteins involved in viral DNA replication.

Among currently-developed adenovirus vectors, replication-deficient adenoviruses lacking the E1 region have been widely used. Meanwhile, an E3 region is removed from a common adenovirus vector, and thus provides a foreign gene insertion site (Thimmappaya, B. et al., *Cell*, 31:543-551 (1982); and Riordan, J. R. et al., *Science*, 245:1066-1073 (1989)). On the other hand, a target nucleotide sequence to be delivered into cells, specifically, is inserted into the deleted E1 region (the E1A region and/or the E1B region, and preferably the E1B region) or E3 region, and more specifically, inserted into the deleted E1 region. The term "deletion" used herein regarding a virus genome sequence not only means complete deletion of the corresponding sequence, but also means partial deletion thereof.

In addition, since adenoviruses may package up to approximately 105% of a wild-type genome, approximately 2 kb may be additionally packaged (Ghosh-Choudhury et al., *EMBO J.*, 6:1733-1739 (1987)). Therefore, the above-mentioned foreign sequence inserted into an adenovirus may be additionally bound to the adenovirus genome.

Adenoviruses have 42 different serotypes and subgroups A to F. Among these, adenovirus type 5 included in subgroup C is the most suitable starting material that can obtain the adenovirus vector of the present invention. Biochemical and genetic information on adenovirus type 5 is well known.

The foreign gene delivered by the adenovirus is replicated by the same method as an episome, and thus has very low genetic toxicity to host cells.

ii. Retroviruses

Retroviruses have been widely used as a gene transfer vector since their own genes can be inserted into a host genome, a large amount of foreign genetic materials can be delivered, and the spectrum of cells to be infected is wide.

To construct a retrovirus vector, instead of a retrovirus sequence, a target nucleotide sequence to be delivered is inserted into a retrovirus genome, thereby producing a non-replicable virus. To produce a virion, a packaging cell line that includes gag, pol and env genes but lacks a long terminal repeat (LTR) and a Ψ sequence is constructed (Mann et al., *Cell*, 33:153-159 (1983)). When a recombinant plasmid including a target nucleotide sequence to be delivered, LTR and a Ψ sequence are introduced into the cell line, the Ψ sequence allows the production of an RNA transcript of the recombinant plasmid, the transcript is packaged into the virus, and the virus is released to a medium (Nicolas and Rubinstein "Retrovirus vectors," In: *Vectors: A survey of molecular cloning vectors and their uses*, Rodriguez and Denhardt (eds.), Stoneham: Butterworth, 494-513 (1988)). The medium containing recombinant retroviruses is collected and condensed to be used as a gene transfer system.

Gene transfer using a second-generation retrovirus vector has been reported. According to Kasahara et al. *Science*, 266:1373-1376 (1994), variants of moloney murine leukemia virus (MMLV) were manufactured, and an erythropoietin (EPO) sequence was inserted into an envelope region, thereby producing a chimeric protein having a novel binding characteristic. The gene transfer system of the present invention may also be manufactured according to construction strategies for the second-generation retrovirus vector as described above.

iii. AAV Vectors

Since an adeno-associated virus (AAV) can be used in the gene transfer system of the present invention because of its ability to infect non-divided cells and various types of cells.

Detailed descriptions on the manufacture and use of the AAV vectors are disclosed in detail in U.S. Pat. Nos. 5,139,941 and 4,797,368.

Typically, AAVs are manufactured by transformation of a plasmid with a target gene sequence adjacent to two AAV terminal repeats (McLaughlin et al., *J. Virol.*, 62:1963-1973 (1988); and Samulski et al., *J. Virol.*, 63:3822-3828 (1989)) and an expression plasmid containing a wild-type AAV coding sequence that does not have a terminal repeat (McCarty et al., *J. Virol.*, 65:2936-2945 (1991)).

iv. Other Virus Vectors

Other virus vectors may also be used as a gene transfer system of the present invention. Vectors derived from vaccinia viruses (Puhlmann M. et al., Human Gene Therapy 10:649-657 (1999); Ridgeway, "Mammalian expression vectors," In: Vectors: A survey of molecular cloning vectors and their uses. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. Gene transfer. New York: Plenum Press, 117-148 (1986) and Coupar et al., Gene, 68:1-10 (1988)), lentiviruses (Wang G. et al., J. Clin. Invest. 104(11):R55-62 (1999)) or herpes simplex viruses (Chamber R., et al., Proc. Natl. Acad. Sci USA 92:1411-1415 (1995)), reoviruses, poxviruses (GCE, NJL, Krupa M, Esteban M., The poxvirus vectors MVA and NYVAC as gene delivery systems for vaccination against infectious diseases and cancer Curr Gene Ther 8(2):97-120 (2008)), Semliki Forest viruses may also be used as a transfer system that can transfer a target nucleotide sequence into cells.

Meanwhile, a foreign gene sequence of a virus used in the present invention is a cancer therapy gene that induces the death of cancer cells, ultimately resulting in degeneration of a tumor, and includes a tumor suppressor gene, an immune regulatory gene [e.g.: a cytokine gene, a chemokine gene and a costimulatory factor: auxiliary molecules necessary for T cell activation such as B7.1 and B7.2)], an antigenic gene, a suicide gene, a cytotoxic gene, a cytostatic gene, a pro-apoptotic gene and an anti-angiogenic gene, but the present invention is not limited thereto.

The suicide gene is a nucleic acid sequence that expresses a material that facilitates the killing of cells by an external factor or induces a toxic condition in cells. A well-known suicide gene is a thymidine kinase (TK) gene (U.S. Pat. Nos. 5,631,236 and 5,601,818). Cells expressing a TK gene product are sensitive to selective death by the administration of gancyclovir. The tumor suppressor gene denotes a gene encoding a polypeptide that inhibits tumorigenesis. The tumor suppressor gene is a naturally-occurring gene in a mammal, and the deletion or inactivation of such a gene has been considered as a prerequisite for tumorigenesis. Examples of the tumor suppressor gene include APC, DPC4, NF-1, NF-2, MTS1, WT1, BRCA1, BRCA2, VHL, p53, Rb, MMAC-1, MMSC-2, a retinoblastoma gene (Lee et al. Nature, 329:642 (1987)), an adenomatous polyposis coli protein (U.S. Pat. No. 5,783,666), a nasopharyngeal tumor suppressor gene located on chromosome 3p21.3 (Cheng et al. Proc. Nat. Acad. Sci., 95:3042-3047 (1998)), a deleted colon cancer (DCC) gene, a member of the INK4a family of tumor suppressor genes including MTS1, CDK4, VHL, p110Rb, p16 and p21 and a therapeutically effective fragment thereof (e.g., p56Rb, p94Rb, etc.). It will be understood by those of ordinary skill in the art that all known anti-oncogenes, other than the exemplified gene, can be used in the present invention.

The term "antigenic gene" used herein refers to a nucleotide sequence that is expressed in target cells and produces a cell surface antigenic protein that can be recognized in an immune system. Examples of such an antigenic gene include a carcinoembryonic antigen (CEA), a prostate specific antigen (PSA), an α-feto protein (AFP), and p53 (WO 94/02167). To be easily recognized by an immune system, the antigenic gene may bind to an MHC type I antigen.

The term "cytotoxic gene" used herein refers to a nucleotide sequence that is expressed in cells and exhibits a toxic effect. Examples of such a cytotoxic gene include nucleotide sequences encoding a *Pseudomonas* exotoxin, a ricin toxin, a diphtheria toxin, etc.

The term "cytostatic gene" used herein refers to a nucleotide sequence that is expressed in cells and suspends the cell cycle during the cell cycle. Examples of such a cytostatic gene may include p21, a retinoblastoma gene, an E2F-Rb fusion protein gene, a gene encoding a cyclin-dependent kinase inhibitor (e.g., p16, p15, p18 and p19), a growth arrest specific homeobox (GAX) gene (WO 97/16459 and WO 96/30385), but the present invention is not limited thereto.

Many therapeutic genes that can be effectively used in treatment of a variety of diseases may also be delivered as means for aiding an antitumor effect via the adenovirus of the present invention. Examples of the therapeutic genes include genes encoding cytokines (e.g., interferon-α, -β, -γ and -δ), interleukins (e.g., IL-1, IL-2, IL-4, IL-6, IL-7, IL-10, IL-12, IL-19 and IL-20) and colony stimulating factors (e.g., GM-CSF and G-CSF), and genes encoding a chemokine group (monocyte chemoattractant protein-1 (MCP-1), monocyte chemoattractant protein-2 (MCP-2), monocyte chemoattractant protein-3 (MCP-3), monocyte chemoattractant protein-4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), EBI1-ligand chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), eotaxin, I-309, human protein HCC-1/NCC-2, human protein HCC-3, and mouse protein C10. In addition, a gene expressing a tissue plasminogen activator (tPA) or urokinase and a gene producing LAL exhibiting a persistent thrombotic effect to prevent hypercholesterolemia are included. In addition, various polynucleotides for treating cystic fibrosis, adenosine deaminase deficiency, viruses such as AIDS, and malignant and inflammatory diseases and conditions are known.

The term "pro-apoptotic gene" used herein refers to a nucleotide sequence that is expressed to induce programmed cell death. Examples of such a pro-apoptotic gene include p53, adenovirus E3-11.6K (derived from Ad2 and Ad5) and adenovirus E3-10.5K (derived from Ad), adenovirus E4 genes, and genes encoding a Fas ligand, TNF-, TRAIL, a p53 pathway gene and a caspase.

The term "anti-angiogenic gene" used herein refers to a nucleotide sequence that is expressed so as to extracellularly release an anti-angiogenetic factor. Examples of the anti-angiogenetic factor include angiostatin, an inhibitor of a vascular endothelial growth factor (VEGF) such as Tie 2 (PNAS, 1998, 95, 8795-800), and endostatin.

In addition, a relaxin or decorin gene defined to be suitable for adenovirus gene therapy by those of ordinary skill in the art is a gene that can be delivered into cells by a gene delivery system.

The above-mentioned target nucleotide sequence may be obtained from a DNA sequence databank such as GenBank or EMBL.

The peptide-viral DNA (or virus) complex or peptide-polymer-viral DNA (or virus) complex of the present invention may be used in treatment of various diseases, and particularly anticancer treatment.

The term "cancer" used herein refers to breast cancer, non-small cell lung cancer, lung cancer, stomach cancer, liver cancer, blood cancer, bone cancer, pancreatic cancer, skin cancer, head and neck cancer, dermal or ocular melanoma, uterine sarcoma, ovarian cancer, rectal cancer, anal cancer, colorectal cancer, tubal cancer, endometrial cancer, uterine cervical cancer, small bowel neoplasm, endocrine carcinoma, bladder cancer, larynx cancer, osteosarcoma, thyroid cancer, brain cancer, colon cancer, vaginal cancer, vulvar cancer, Hodgkin's disease, esophageal cancer, adrenal gland cancer, penile carcinoma, acute leukemia, lymphocyte lymphoma, ureteral cancer, renal pelvic carcinoma, a central nervous system (CNS) tumor, primary CNS lymphoma, a spinal cord tumor, nasopharyngeal cancer, brain stem glioma, pituitary adenoma, parathyroid cancer, kidney cancer, soft tissue sarcoma, a urethral tumor, prostate cancer, bronchial cancer or bone marrow cancer.

The term "treatment" used herein refers to (i) prevention of the formation of cancer cells; (ii) inhibition of cancer-associated diseases or disorders according to the removal of cancer cells; and (iii) alleviation of cancer-associated diseases or disorders according to the removal of cancer cells. Therefore, the term "therapeutically effective amount" used herein refers to an amount sufficient for achieving the pharmaceutical effect.

A pharmaceutically acceptable carrier included in the composition of the present invention is conventionally used in formulation, and may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but the present invention is not limited thereto. The pharmaceutical composition of the present invention may further include a lubricant, a wetting agent, a sweetening agent, a flavoring agent, an emulsifier, a suspension, a preservative, etc., other than the above-mentioned components.

The pharmaceutical composition of the present invention may be administered parenterally, for example, intravenously, intraperitoneally, intramuscularly, subcutaneously or locally. The pharmaceutical composition may be administered intraperitoneally to treat ovarian cancer, and may be administered into a portal vein to treat liver cancer. The pharmaceutical composition may be directly injected into a tumor mass, in the case of breast cancer, and may be directly injected through an enema to treat colorectal cancer.

A suitable dosage of the pharmaceutical composition may vary according to parameters such as a formation method, an administration method, a patient's age, body weight and sex, the severity of a disease symptom, a diet, administration time, administration route, excretion speed and reaction sensitivity, and an effective dosage for desired treatment may be easily determined and prescribed by an ordinary skilled doctor. Generally, the pharmaceutical composition of the present invention includes a polymer-virus complex at $1 \times 10^5$-$1 \times 10^{15}$ pfu/ml, and is conventionally injected at $1 \times 10^{10}$ pfu every other day for 2 weeks.

The pharmaceutical composition of the present invention may be prepared by unit-dose packaging or multi-dose packaging after being formulated using a pharmaceutically acceptable carrier and/or excipient according to a method that can be easily implemented by those or ordinary skill in the art. Here, a dosage form may be a solution in an oil or aqueous medium, a suspension or an emulsion, an extract, a powder, a granule, a tablet or a capsule, and the pharmaceutical composition of the present invention may further include a dispersant or a stabilizer.

The pharmaceutical composition of the present invention may be used alone, or in combination with conventional chemotherapy or radiation therapy, and such a combination method can be more effectively used in cancer treatment. Medications for chemotherapy that can be used in combination with the composition of the present invention include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. Examples of radiation therapy that can be used in combination with the composition of the present invention include X-ray radiation and γ-ray radiation.

According to yet another aspect of the present invention, the present invention provides a method for improving intracellular delivery efficiency of a bioactive substance using a composition containing a peptide of SEQ ID NO: 1 or a modified peptide thereof.

According to yet another aspect of the present invention, the present invention provides a method for increasing intracellular delivery efficiency of a bioactive substance using a composition including a biocompatible polymer and a peptide of SEQ ID NO: 1 or a modified peptide thereof.

The term "bioactive substance" used herein refers to a physiological function regulator having biological activity, and a substance that can be applied to treatment of all diseases caused by the imbalance or dysfunction of a physiological function in terms of the purpose of the present invention. The bioactive substance may be a nucleic acid, a peptide, a polypeptide, an antibody, a chemical compound (chemotherapeutic) or a virus, but the present invention is not limited thereto.

Since the method of the present invention uses the above-described peptide or peptide-polymer complex, a common content will be omitted to avoid excessive complexity in the specification.

Advantageous Effects

Characteristics and advantages of the present invention are summarized as follows:

(a) The present invention provides a composition for efficiently delivering the bioactive substance of the present invention into cells.

(b) In addition, the present intention provides a pharmaceutical composition, which includes the composition and viral DNA or virus for treating cancer.

(c) In addition, the present invention provides a method for efficiently delivering a bioactive substance into cells.

(d) Since a peptide or peptide-polymer complex of the present invention exhibits higher intracellular delivery efficiency than a conventional method, it can be effectively used as a system for intracellular delivery of various therapeutics.

DESCRIPTION OF DRAWINGS

FIG. 7 represents images of endosome escape of an Ad DNA-polymer-peptide complex (Ad pDNA-PAM-ABP-VI-9R), observed by fluorescence microscopy.

FIG. 8 is a chart summarizing the sequences of modified peptides.

FIG. 16 represents the effects of an Ad DNA-polymer-peptide complex (Ad pDNA-(PAM-ABP)-peptide), in which FIG. 16A represents the result that verifies viral proliferation capability; and FIG. 16B represents the result that confirms oncolytic capability.

FIG. 20 shows the effect of an Ad pDNA-polymer-dimer peptide complex in a PC-3 cell line, in which FIG. 20A represents the result that confirms viral proliferation capability; and FIG. 20B represents the result that confirms oncolytic capability.

FIG. 21 shows the effect of an Ad pDNA-polymer-dimer peptide complex in a HapT1 cell line, in which FIG. 21A represents the result that confirms viral proliferation capability; and FIG. 21B represents the result that confirms oncolytic capability.

which 9 amino acids (arginine) were connected to the C-terminus of a peptide (SEQ ID NO: 1) consisting of 13 amino acids derived from adenovirus protein VI and a polymer. To this end, first, adenovirus DNA was added to PBS buffer, and after a weight ratio was calculated, a peptide was added, followed by reacting at room temperature for 10 minutes. Afterward, the polymer was added again at various weight ratios, and reacted at room temperature for 15 minutes, thereby preparing an Ad pDNA-polymer-VI-9R complex. As the polymer, an arginine-grafted bio-reducible poly(CBA-DAH) polymer (ABP) and a polyamidoamine (PAMAM) dendrimer-conjugated PAM-ABP were used, and their structures are shown as follows (Journal of Controlled Release, Vol 160 592-600 2012).

[Formula 1]

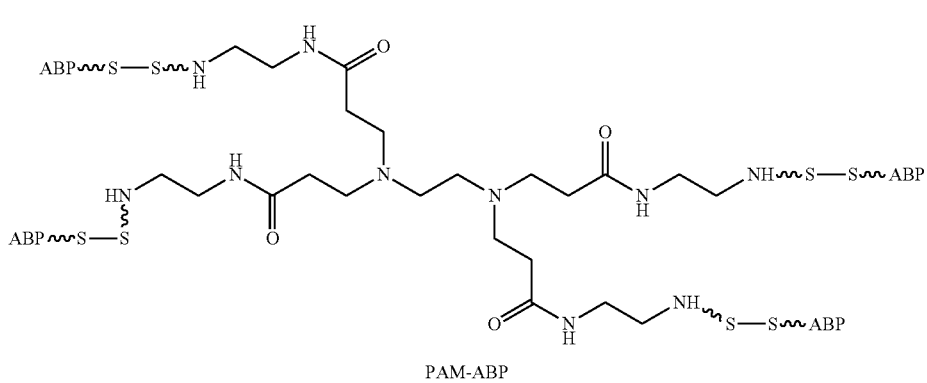

PAM-ABP

Figure 29:
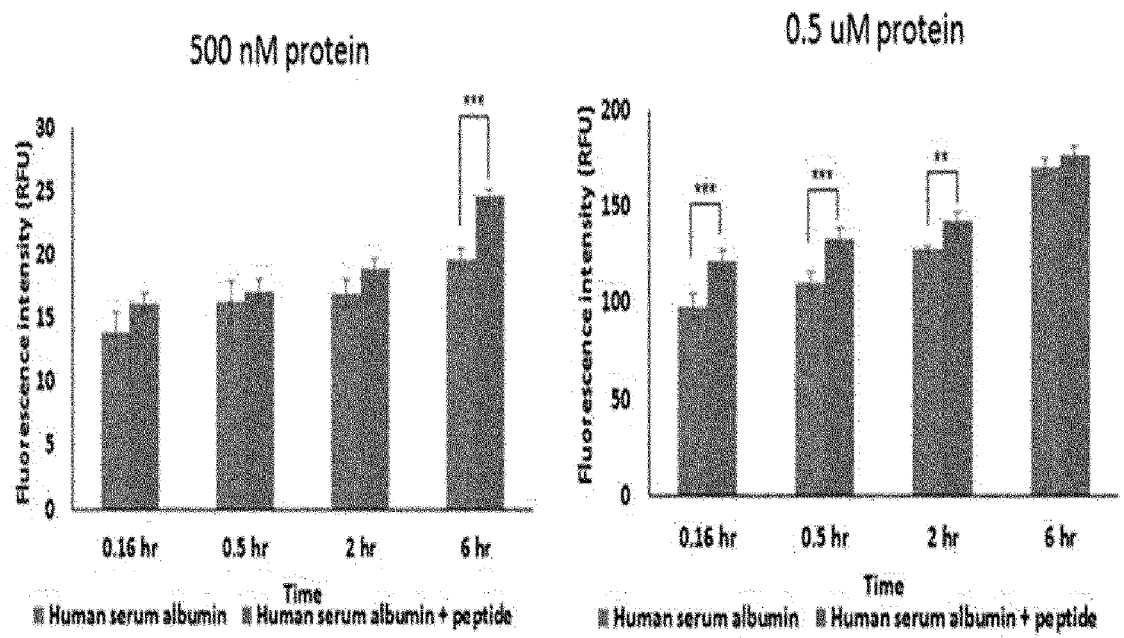

FIG. 29 shows the cellular uptake efficiency of protein (human serum albumin)/peptide complexes, in which FIG. 29A shows the cellular uptake efficiency obtained using 50 nM of the protein, and FIG. 29B shows the cellular uptake efficiency obtained using 0.5M of the protein.

Figure 30:
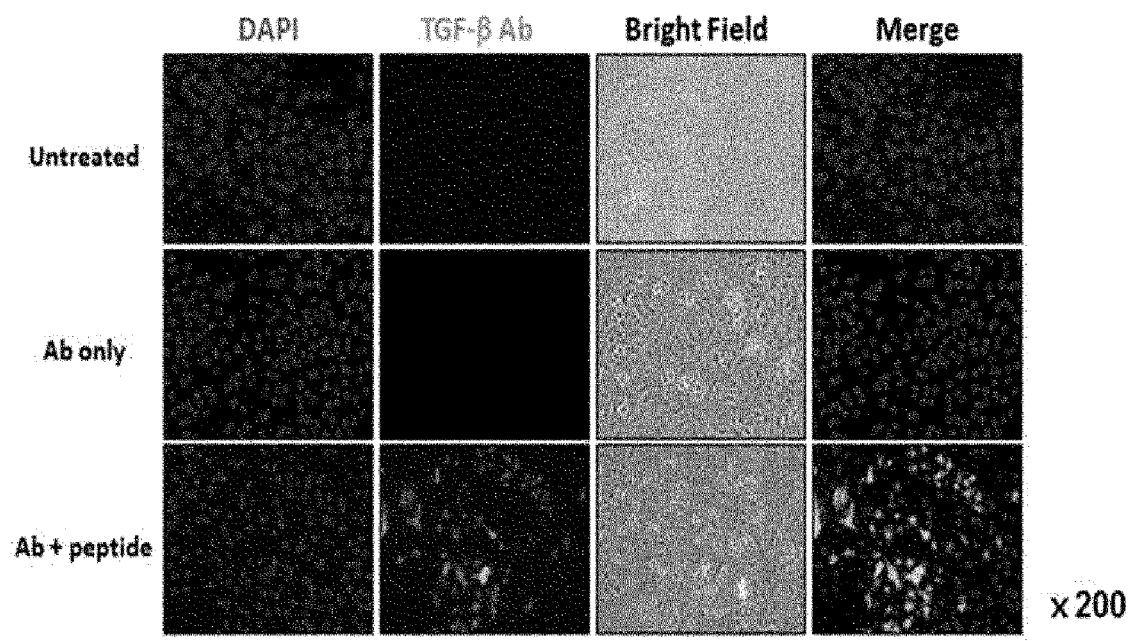

FIG. 30 represents the result that confirms the intracellular delivery efficiency of an antibody/peptide complex (antibody (rabbit polyclonal to TGF beta 1)/peptide complex).

MODES OF THE INVENTION

Hereinafter, the present invention will be described in further detail with respect to examples. These examples are only provided to more fully describe the present invention, and it is obvious to those of ordinary skill in the art that the scope of the present invention is not limited to these examples, according to the scope of the present invention.

EXAMPLES

Example 1: Analysis of Physical Properties of Peptide-Polymer Complex

It was intended to enhance the intracellular delivery efficiency of adenovirus DNA using a peptide (VI-9R) in Afterward, it was intended to identify conditions for forming a complex from DNA by binding a peptide-polymer complex with Ad pDNA. The weight ratio of adenovirus plasmid DNA (Ad pDNA) to VI-9R was fixed to 1:10 for a reaction, and then the weight ratio of DNA to the polymer was adjusted to 1:1, 1:5, 1:10, 1:15 and 1:20 so as to confirm a degree of binding the Ad pDNA-polymer-VI-9R complex. The optimal conditions for forming the Ad pDNA-polymer-VI-9R complex were determined, and a gel retardation assay was performed to analyze physical properties.

Figure 1:
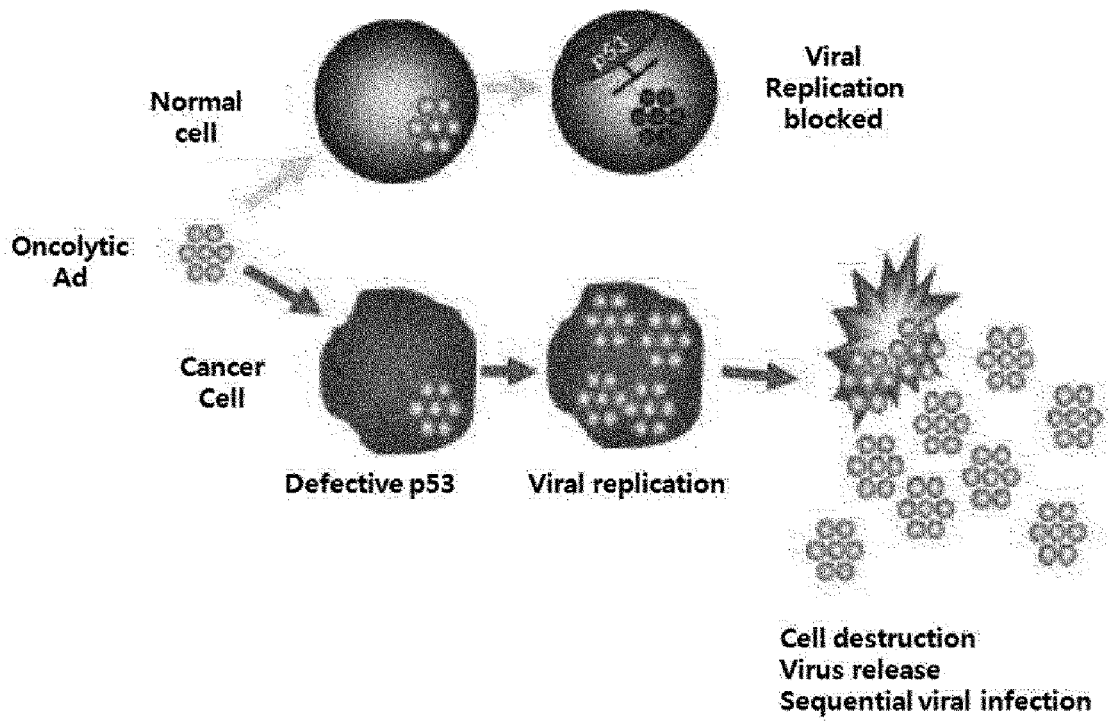
FIG. 1 is a schematic diagram illustrating the cancer cell-specific oncolytic effect of a tumor-selective oncolytic adenovirus.
Figure 2:
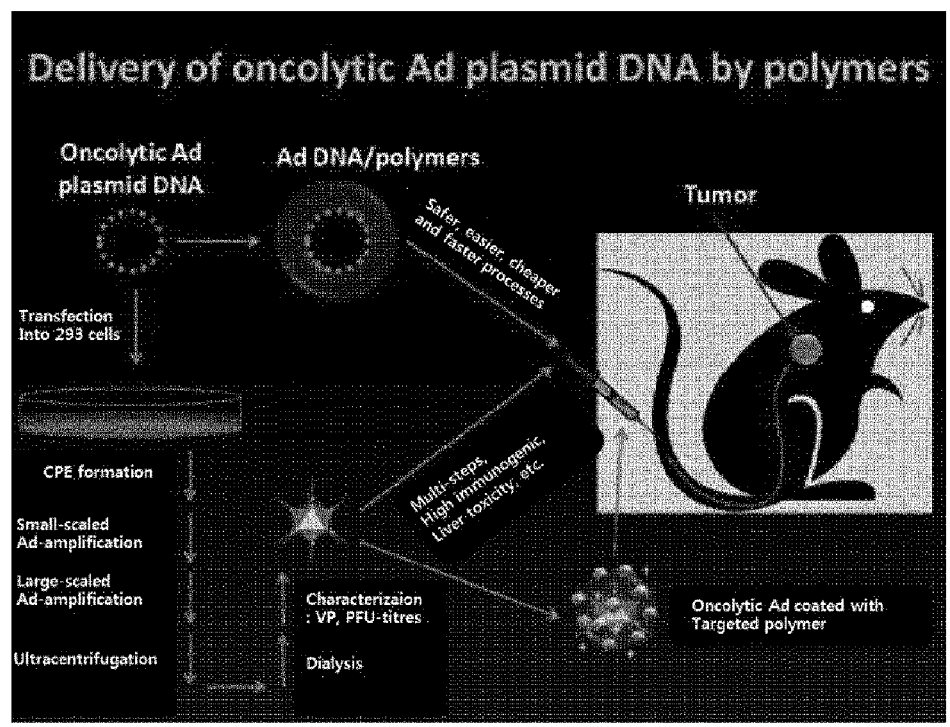
FIG. 2 is a schematic diagram illustrating a comparison of systemic administration using an adenovirus plasmid DNA-polymer with administration using an adenovirus itself.
Figure 3:
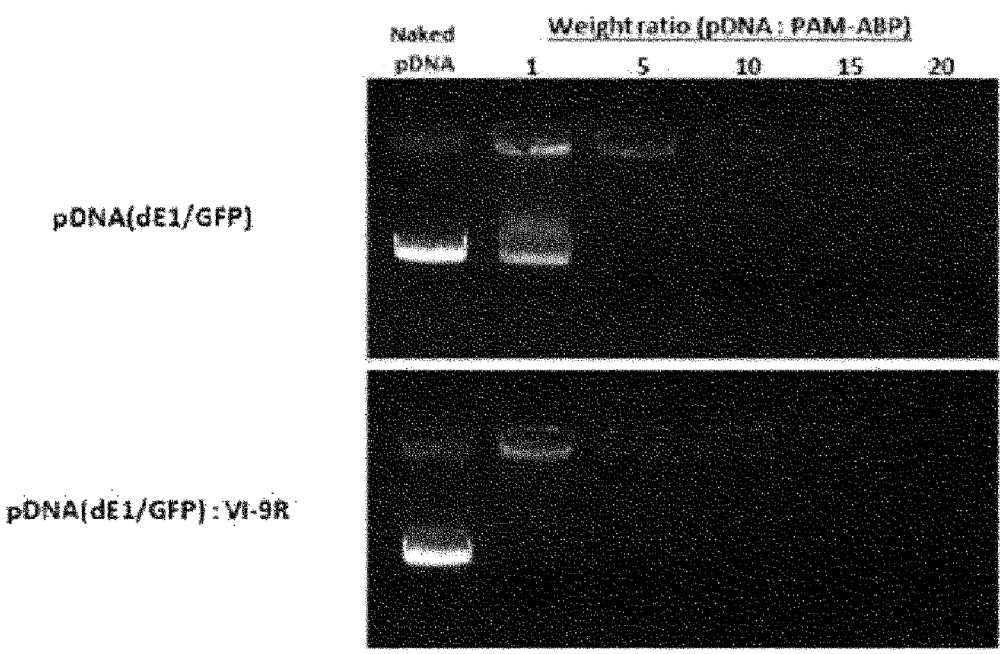
FIG. 3 is the result of identifying the DNA condensation conditions for an Ad DNA-polymer-peptide complex (Ad pDNA-polymer-VI-9R).
Figure 4:
FIG. 4 represents images for comparing the intracellular gene delivery efficiency of an Ad DNA-polymer-peptide complex (Ad pDNA-PPCBA-VI-9R).

As a result of the analysis, from when the weight ratio of DNA:polymer was 1:1, it was confirmed that DNA condensation sufficiently occurs by loading adenovirus DNA in the polymer-peptide complex (FIG. 4). Therefore, when VI-9R was used in combination with a polymer, it was confirmed that the adenovirus DNA was sufficiently loaded in the polymer-peptide complex even with a small amount of the polymer.

Example 2: Confirmation of Intracellular Gene Delivery Efficiency of Ad pDNA-Polymer-VI-9R Complex In Example 2, as a polymer, mPEG-b-Pip-CBA (PPCBA) which has biodegradability and pH sensitivity was used, and its structure is shown as follows (Biomaterials, Vol 41 53-68 2015).

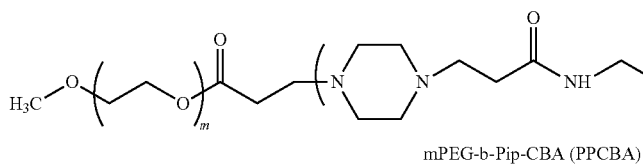

mPEG-b-Pip-CBA (PPCBA)

To confirm the intracellular gene delivery efficiency of an Ad pDNA-PPCBA-VI-9R complex, first, adenovirus DNA was added to PBS buffer using plasmid DNA of a GFP-expressing replication-deficient adenovirus (pdE1/GFP), after a weight ratio was calculated, a peptide was added to the same tube, followed by reacting at room temperature for 10 minutes. Afterward, the polymer was added, and reacted at room temperature for 15 minutes, thereby preparing an Ad pDNA-polymer-VI-9R complex. A 293A cell line reaching 60 to 70% confluence after inoculating the cells into a 24-well plate was treated with pdE1/GFP-PPCBA and a pdE1/GFP-PPCBA-VI-9R complex, and after 72 hours, GFP expression was observed by fluorescence microscopy.

As a result of the observation, in the case of pdE1/GFP-PPCBA, GFP expression was not observed at all, but when cells were treated with the pdE1/GFP-PPCBA-VI-9R complex, considerably increased GFP expression was observed (FIG. 4). From the above result, it was confirmed that the pdE1/GFP-PPCBA-VI-9R complex in which the polymer was conjugated with VI-9R can overcome low gene delivery efficiency, which is the limit of the complex (pdE1/GFP-PPPCBA) in which viral DNA was conjugated with only a polymer, and considerably increase intracellular gene delivery efficiency.

Example 3: Confirmation of Virus Proliferation Capability of Ad pDNA-Polymer-VI-9R Complex In Example 3, PPCBA was used as a polymer, and tumor-selective oncolytic adenovirus RdB/GFP viral DNA, that is, Ad pDNA (RdB/GFP), expressing GFP was used as adenovirus DNA. To confirm the viral proliferation capability of an Ad pDNA (RdB/GFP)-PPCBA-VI-9R complex, an A549 cell line was inoculated into a 12-well plate, and after 24 hours, the cells were treated with each of naked Ad pDNA, an Ad pDNA-PEI 25K complex and the Ad pDNA-PPCBA-VI-9R complex. After 72 hours, a culture solution was collected, and the number of adenovirus particles was determined by Q-PCR.

Figure 5:
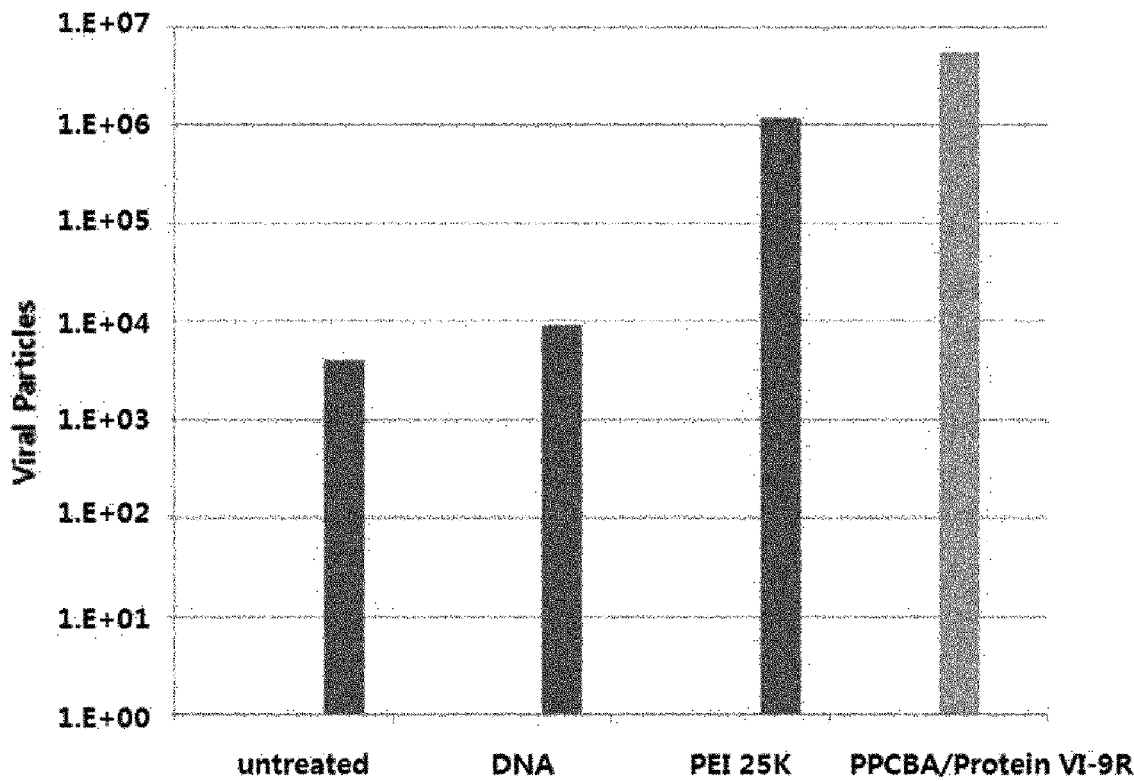
FIG. 5 is a graph for analyzing the viral proliferation capability of an Ad DNA-polymer-peptide complex (Ad DNA-polymer-VI-9R).

As a result of the analysis, it was confirmed that, when only naked Ad pDNA was treated, virus production was determined at a basal level ($9.2 \times 10^3$ VP), and when the Ad pDNA-PPCBA-VI-9R complex was treated, virus production ($5.5 \times 10^6$ VP) was increased 596 times, as compared with the case in which the naked Ad pDNA was treated (FIG. 5). This shows that the virus production was increased 4.6 times, compared with the case in which the Ad pDNA-PEI 25K complex was treated as a positive control ($1.2 \times 10^6$ VP). This result shows the probability of a very high increase in virus production due to the characteristic of the Ad pDNA-PPCBA-VI-9R complex in which viral proliferation is very successfully performed in cancer cells, and then the proliferated adenoviruses are sequentially proliferated in tumor cells.

Example 4: Confirmation of Cellular Uptake Efficiency of Ad pDNA by Ad pDNA-Polymer-VI-9R Complex In Example 4, PAM-ABP was used as a polymer. To confirm cellular uptake efficiency of Ad pDNA is increased by an Ad pDNA (dE1/GFP)-PAM-ABP-VI-9R complex, a 293A cell line was inoculated into a 12-well plate and grown to 60 to 70% confluence, and after 24 hours, the cells were treated with Ad pDNA-PEI, Ad pDNA-PAM-ABP and the Ad pDNA-PAM-ABP-VI-9R complex using FITC-labeled Ad plasmid DNA (FITC-pDNA). After 2 hours, FITC-labeled-pDNA contents absorbed into the cells were compared by FACS.

Figure 6:
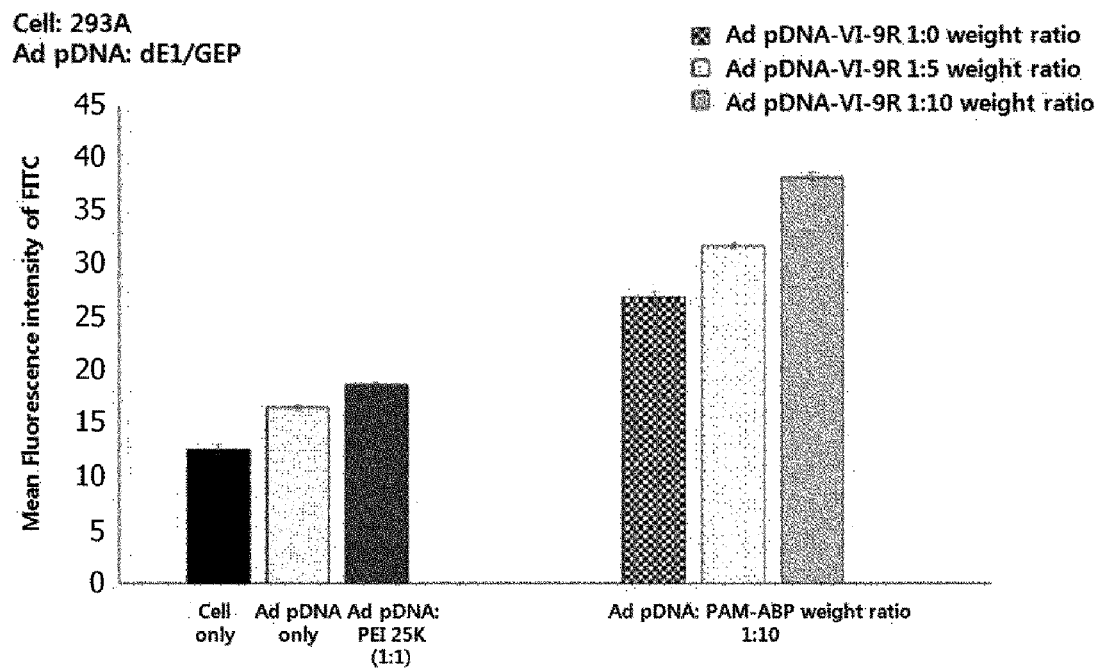
FIG. 6 is a graph for analyzing the cellular uptake efficiency of an Ad DNA-polymer-peptide complex (Ad pDNA-polymer-VI-9R).

As a result of the analysis, a complex formed by reacting FITC-labeled Ad pDNA with PEI, PAM-ABP and PAM-ABP/VI-9R (the weight ratio of pDNA:VI-9R 1:5 or 1:10) was transfected into the cells, and after 2 hours, FACS was performed. As a result of the analysis, when PAM-ABP was used, the cellular uptake efficiency was considerably increased as compared with the Ad pDNA-PEI used as the positive control. Particularly, when the Ad pDNA-PAM-ABP-VI-9R complex was used, the cellular uptake efficiency was improved 1.2 to 1.4 times, as compared with the case of PAM-ABP using only the polymer (FIG. 6). Such a result seems that the improvement in cellular uptake efficiency of the Ad pDNA-PAM-ABP/VI-9R complex is caused by increased cell permeability due to binding of VI-9R with pDNA and PAM-ABP.

Example 5: Endosome Escape Effect in Cancer Cells of Ad pDNA-Polymer-VI-9R Complex In Example 5, PAM-ABP was used as a polymer, and pdE1-GFP was used as adenovirus DNA. Endosomal sequestration of a biological agent delivered into cells acts as a critical obstacle to enhancing gene delivery efficiency. Meanwhile, it has been known that a polymeric material containing an amine, sulfonamide or carboxylic acid exhibits a function of allowing the biological agent delivered into cells to escape from an endosome by destruction of an endosome membrane, resulting in increased non-viral gene delivery efficiency and increased intranuclear delivery efficiency of a chemotherapeutic. In Example 5, to verify the endosome escape effect of viral DNA by VI-9R, fluorescent staining of cells was performed. A HEK293 ($1 \times 10^5$ cells) cell line was inoculated into 6-well plate with a cover glass, and after 24 hours, the nucleus and the endosome were stained with DAPI and lysotracker, respectively. Afterward, a conjugate of GFP-expressing adenovirus DNA (pdE1-GFP) and PAM-ABP or a PAM-ABP-VI-9R complex, that is, Ad pDNA-PAM-ABP or Ad pDNA-PAM-ABP-VI-9R, was treated at 2 μg/mL, and after 4 hours, the cells were fixed with a 4% formaldehyde solution to observe the endosome escape effect using a confocal microscope.

As a result of the observation (FIG. 7), it can be seen that, in the case of the cells treated with Ad pDNA-PAM-ABP, the lysotracker and GFP overlapped, and when only Ad pDNA-PAM-ABP was bound to viral DNA and treated, the escape efficiency of viral DNA from an endosome was low. However, it was observed that, when the Ad pDNA-PAM-ABP-VI-9R complex was treated, GFP and the fluorescence of the lysotracker did not overlap, and the virus (GFP) was translocated into the nucleus, which means that the Ad pDNA-PAM-ABP-VI-9R complex improved the endosome escape effect of the viral DNA. Such a result shows that, when Ad pDNA-PAM-ABP was used alone, the limitations such as a low endosome escape effect and the degradation in gene delivery efficiency thereby can be overcome due to the use of the polymer-VI-9R complex.

Example 6: Modification of Ad Protein VI-Derived Peptides and Physical Properties Thereof To further improve the gene delivery efficiency of VI-9R confirmed in the above-described example, the adenovirus virus VI-derived peptide (SEQ ID NO: 1) was modified in various forms (FIG. 8). That is, a hydrophobic amino acid was further added or a conventionally known cell-permeating peptide (CPP), TAT, was further connected to the N-terminus of the peptide. To analyze the physical properties of the modified peptides, each peptide was put into a cuvette with a total volume of 1 ml at 10 μg/ml, and surface charge values of the peptides dissolved in pH 7.4 PBS and pH 6.4 PBS were measured using a Zeta-sizer.

Figure 9:
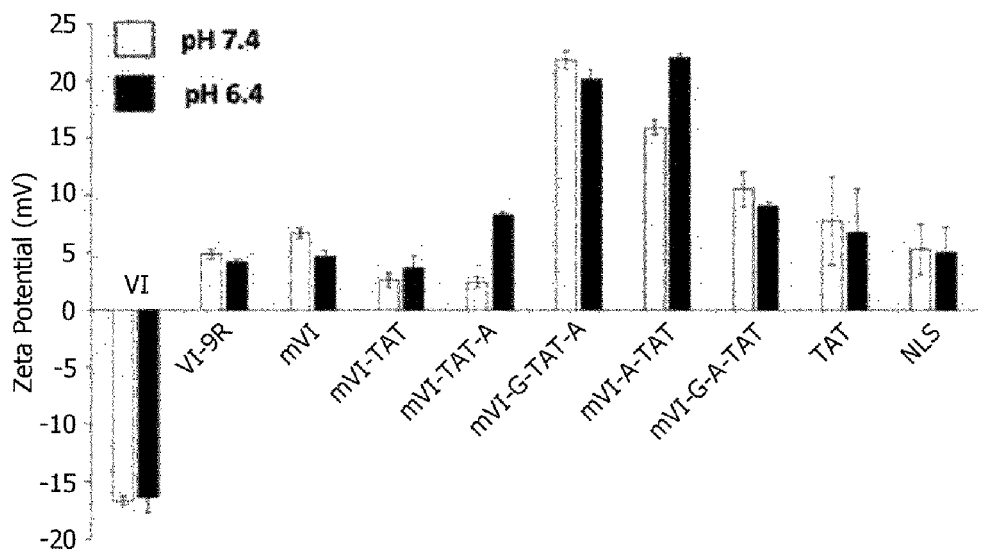
FIG. 9 is a graph for comparing the surface charges of peptides according to a pH change.

As a result of the Zeta potential analysis (FIG. 9), VI-9R exhibited a negative charge of 16.6±0.41 mV in an environment of pH 7.4, and the VI-9R peptide exhibited a positive charge of 4.87±0.42 mV by further addition of an R sequence. Compared with the VI peptide, the surface charge of modified VI (mVI) had changed to positive. In addition, as a pH was reduced, the surface charge of mVI-TAT-A or mVI-A-TAT to which a bipolar amino acid glutamic acid (E) was added was increased.

Example 7: Intracellular Gene Delivery Efficiency of Ad pDNA-Polymer-Peptide Complex In Example 7, PPCBA and PAM-ABP were used as polymers. To confirm the intracellular gene delivery efficiency of the Ad pDNA(dE1/GFP)-PPCBA-peptide complex, a 293A cell line was inoculated into a 24-well plate and grown to 60 to 70% confluence, and the cells were treated with each of 6 types of modified peptides and the Ad pDNA-PPCBA-peptide complex. VI-9R, NLS, TAT and a protamine were used as controls, and treated with the complex, and after 24 hours, GFP expression was observed using fluorescence microscopy.

Figure 10:
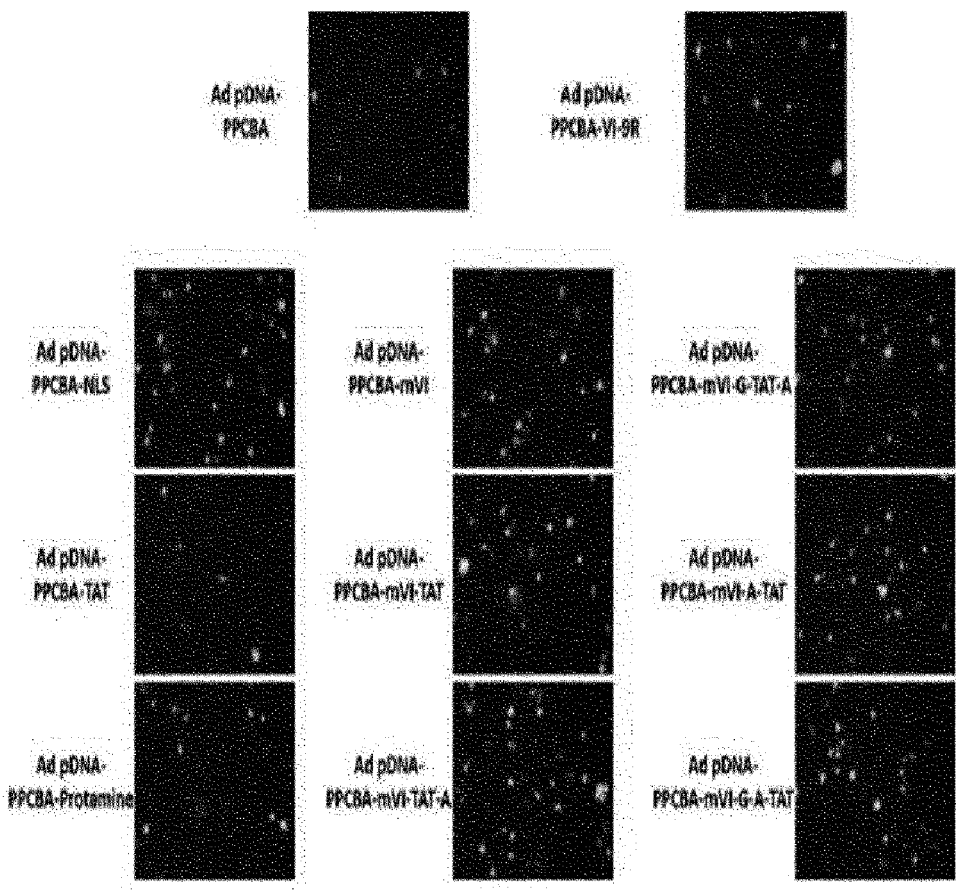
FIG. 10 represents images for comparing the intracellular gene delivery efficiency of Ad DNA-polymer-peptide complexes (Ad pDNA-PPCBA-R-peptide).

As a result of the analysis, when the Ad pDNA-PPCBA-VI-9R complex was treated, compared with when Ad pDNA or Ad pDNA-PPCTBA was treated, the GFP expression was considerably increased. In addition, when each of the 6 types of modified peptides such as mVI, mVI-TAT, mVI-TAT-A, mVI-G-TAT-A, mVI-A-TAT or mVI-G-A-TAT was treated after forming a complex with Ad pDNA-PPCTBA, compared with when VI-9R was not modified, the GFP expression was increased (FIG. 10).

To confirm the intracellular gene delivery efficiency of the Ad pDNA(dE1/GFP)-PAM-ABP-peptide complex using another polymer, that is, PAM-ABP, a 293A cell line was inoculated into a 24-well plate and grown to 60 to 70% confluence, and after 24 hours, treated with each of the Ad pDNA-PAM-ABP-peptide complexes formed using the 6 types of modified peptides mVI, mVI-TAT, mVI-TAT-A, mVI-G-TAT-A, mVI-A-TAT and mVI-G-A-TAT. Ad pDNA-PAM-ABP/TAT and Ad pDNA/PEI25K were used as controls and treated with the complex, and after 4 days, GFP expression was observed using fluorescence microscopy.

Figure 11:
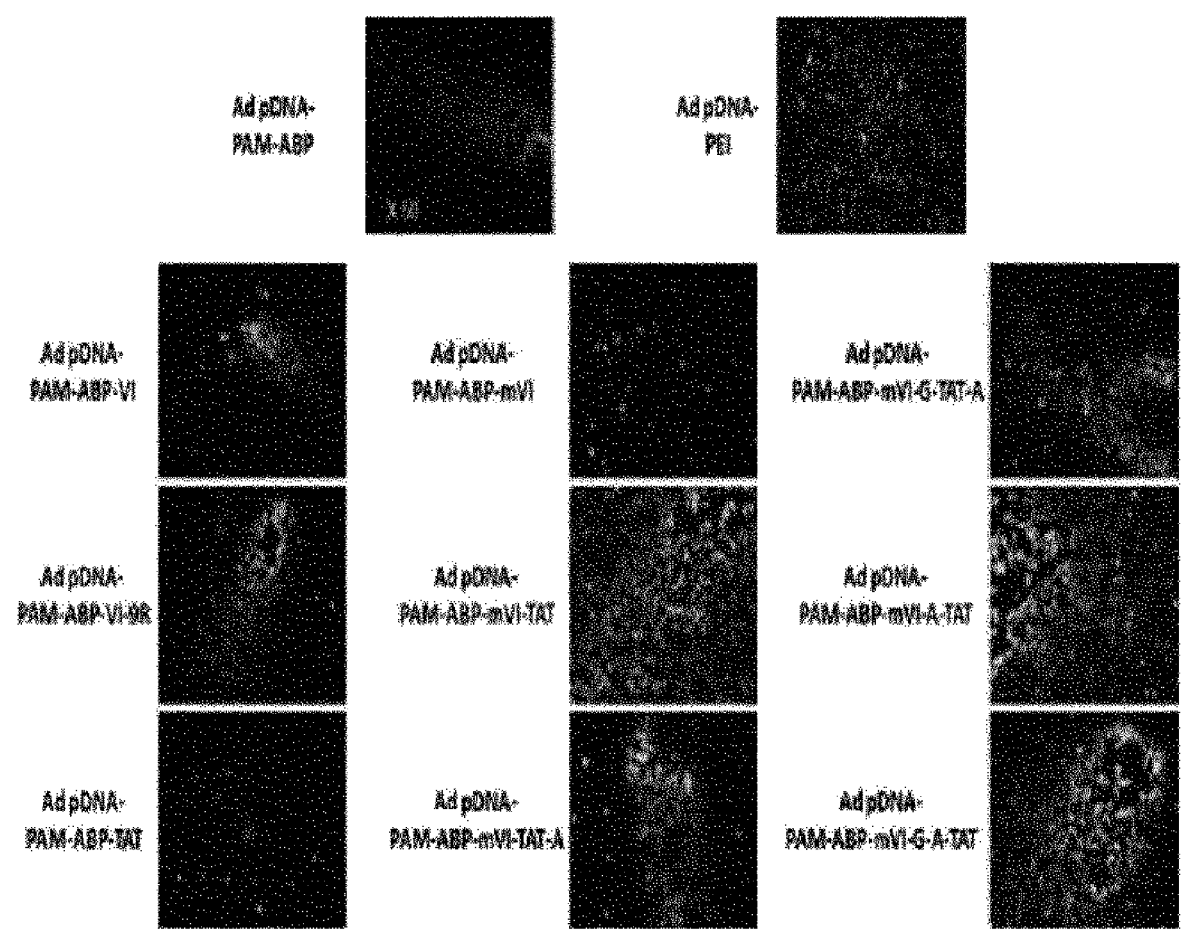
FIG. 11 shows the results that verify the intracellular gene delivery efficiency of Ad DNA-polymer-peptide complexes (Ad pDNA-PAM-ABP-peptide).

As a result of the analysis, when the Ad pDNA-PAM-ABP-peptide complex was treated, compared with when Ad pDNA-PAM-ABP was treated, the gene delivery efficiency was increased (FIG. 11). Particularly, compared with when Ad pDNA-PAM-ABP/TAT was treated as a positive control, when the Ad pDNA-PAM-ABP-peptide complex in which PAM-ABP was conjugated with each of the 6 types of modified peptides mVI, mVI-TAT, mVI-TAT-A, mVI-G-TAT-A, mVI-A-TAT and mVI-G-A-TAT was treated, the gene delivery efficiency was considerably increased. Such a result shows that the modified peptides can increase the gene delivery efficiency of the Ad pDNA-PPCBA-peptide complexes.

Example 8: Increase in Cellular Uptake Efficiency of Ad pDNA by Ad pDNA-Polymer-Peptide Complex In Example 8, PAM-ABP was used as a polymer. To confirm the cellular uptake efficiency of the Ad pDNA-PAM-ABP-peptide complex, an A549 lung cancer cell line was inoculated into a 12-well plate and grown to 60 to 70% confluence, and after 24 hours, treated with FITC-labeled Ad pDNA (dE1/GFP) and PAM-ABP-VI-9R or various types of PAM-ABP-modified peptide complexes (mVI, mVI-TAT, mVI-TAT-A, mVI-G-TAT-A, mVI-A-TAT and mVI-G-A-TAT). Ad pDNA-PAM-ABP-NLS and Ad pDNA-PAM-ABP-TAT were used as controls and treated with the complexes, and after 30 minutes, amounts of FITC-pDNA absorbed into the cells were compared and analyzed by FACS.

Figure 12:
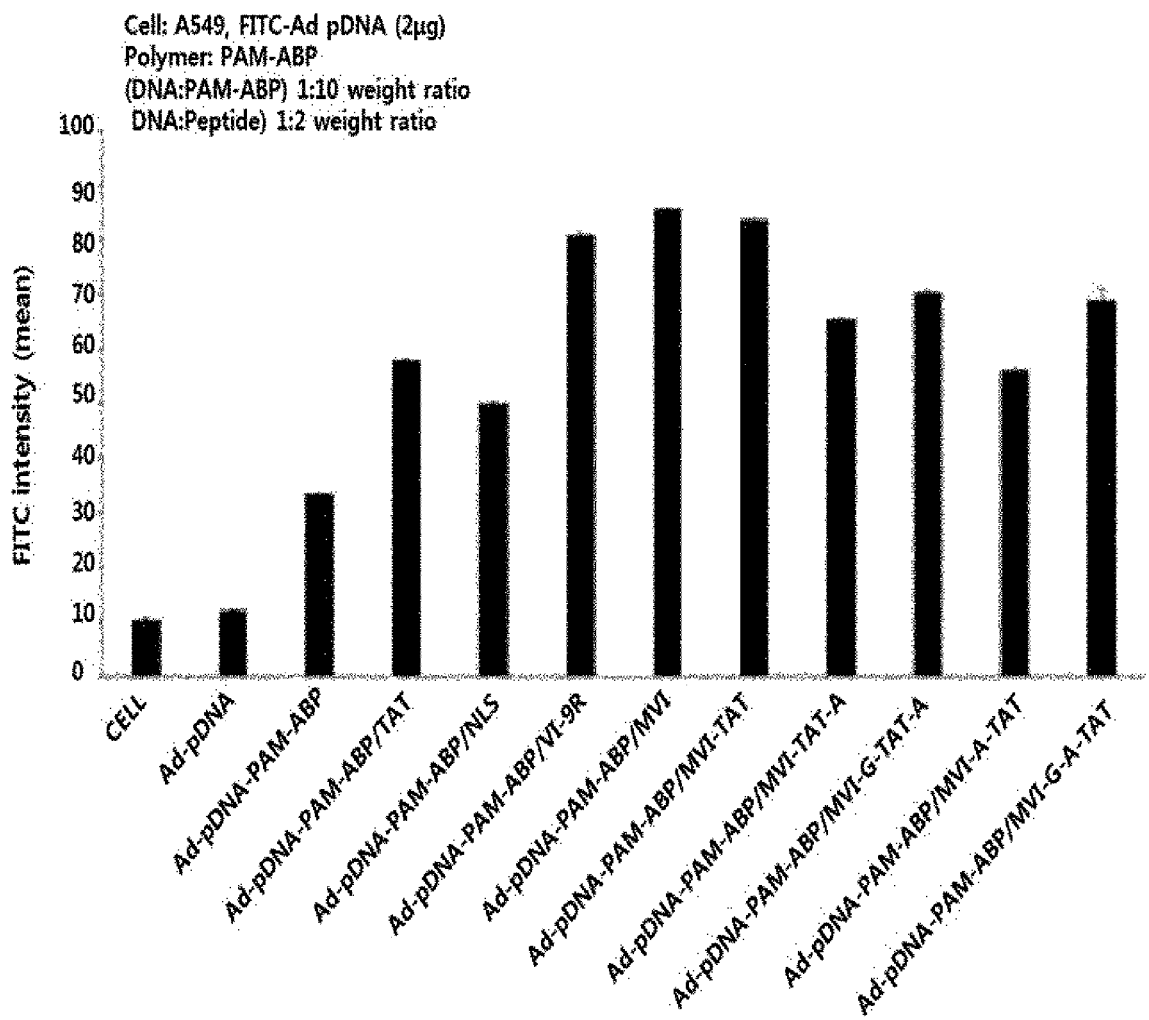
FIG. 12 is a graph for comparing and analyzing the cellular uptake efficiency of various Ad DNA-polymer-peptide complexes.

The cellular uptake efficiencies of VI-9R and Ad pDNA-PAM-ABP-peptide complexes formed using the 6 types of modified peptides (mVI, mVI-TAT, mVI-TAT-A, mVI-G-TAT-A, mVI-A-TAT and mVI-G-A-TAT) were increased 2.4, 2.6, 2.5, 2.0, 2.1, 1.6 and 2.1 times, respectively, as compared with the case of Ad pDNA-PAM-ABP as the control (FIG. 12). Particularly, compared with other positive controls, such as Ad pDNA-PAM-ABP/NLS and Ad pDNA-PAM-ABP/TAT, they also showed considerably increased cellular uptake efficiencies.

Example 9: Analysis of DNA Condensation Efficiency by Ad pDNA-Peptide Complex

To confirm the DNA condensation efficiency of an Ad pDNA-peptide complex, DNA condensation efficiency was confirmed by PicoGreen staining. After a PicoGreen dye (100 μl) which is known to specifically bind to DNA was reacted with various forms of Ad pDNA-peptide complexes (1 μg), a degree of fluorescence expression was confirmed using a microplate reader, and condensation efficiency was confirmed. The higher the DNA condensation is, the lower the degree of fluorescence expression.

Figure 13:
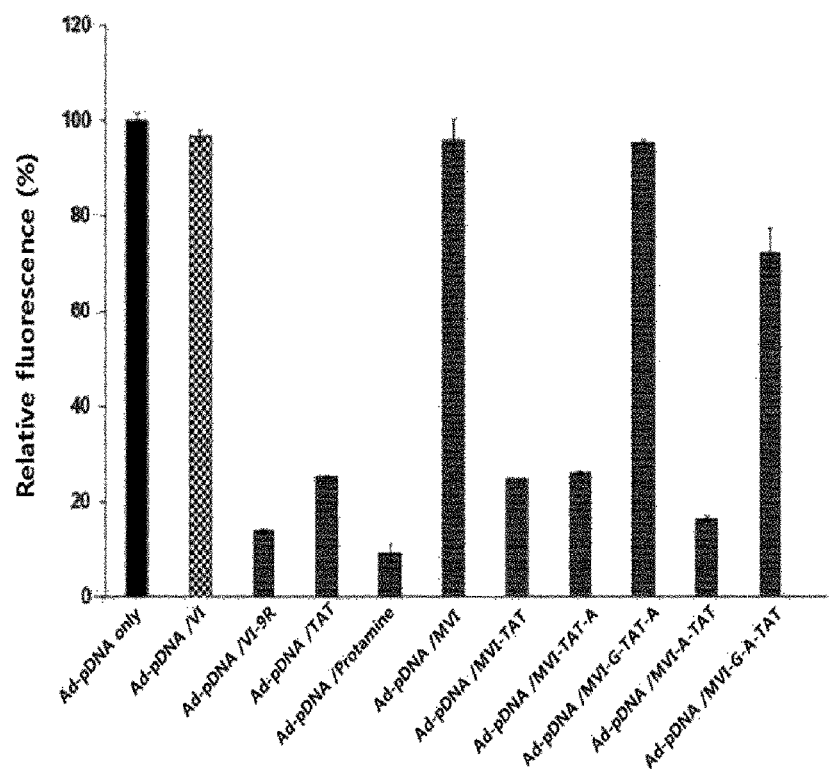
FIG. 13 is a graph for comparing DNA condensation efficiency between various types of modified peptides and Ad pDNA complexes.

As a result of the analysis, in the case of Ad pDNA-VI, DNA condensation hardly occurred, and among modified peptides, it was confirmed that in the cases of mVI-TAT, mVI-TAT-A and mVI-A-TAT, DNA condensation was induced, but in the cases of mVI, mVI-G-TAT-A and mVI-G-A-TAT, DNA condensation was not induced (FIG. 13).

Example 10: Membrane Lytic Activity Improved by Peptide

Endosomal escape is a phenomenon in which DNA escapes by lysis of a membrane in an endosome, and PI staining was performed to confirm a degree of destruction of the membrane by an Ad-polymer-peptide complex. Each of the peptides used herein was reacted at 50 nM for 30 minutes in a 37° C. incubator. Afterward, 100 µg of PI was reacted for 10 minutes at 37° C., and after a medium change, a result was checked using fluorescence microscopy. The higher the degree of membrane lysis is, the higher the degree of fluorescence expression.

Figure 14:
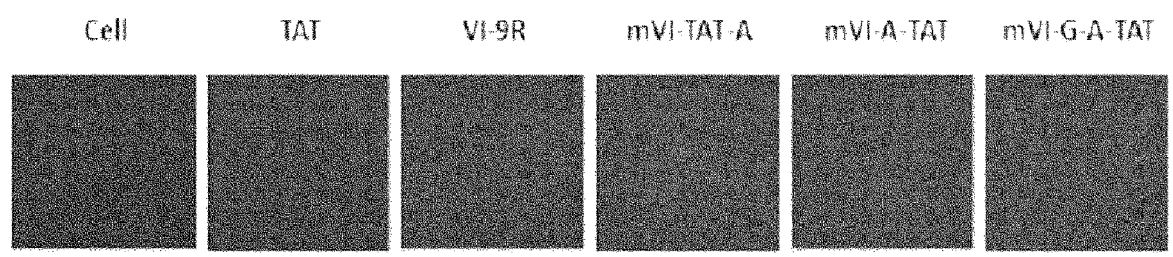
FIG. 14 represents images for comparing membrane lytic activity by various types of modified peptides.

As a result of the analysis, it was confirmed that, when a peptide used as a positive control, TAT, was treated, membrane lysis hardly occurred, but when peptides (VI-9R, mVI-TAT-A, mVI-A-TAT and mVI-G-A-TAT) were treated, membrane lysis efficiency was considerably improved (FIG. 14). To this end, the modified peptides are expected to exhibit an improved endosomal escape effect.

Example 11: Nuclear Localization Increased by Ad pDNA-Polymer-Peptide Complex In Example 11, PAM-ABP was used as a polymer. To compare nuclear localization improved by an Ad pDNA-polymer-peptide complex, an A549 cell line was inoculated into a 24-well plate. After Ad DNA was labeled with FITC, an Ad pDNA-PAM-ABP complex and Ad pDNA-PAM-ABP-peptides (mVI, mVI-TAT, mVI-TAT-A, mVI-G-TAT-A, mVI-A-TAT, mVI-G-A-TAT, VI, VI-9R, TAT and NLS) complexes were prepared using the FITC-labeled Ad DNA, followed by treating these complexes 24 hours after cell inoculation. Four hours after the treatment of Ad pDNA-PAM-ABP-peptide complexes, the cytoplasm and the nucleus were subjected to measurement at Ex/Em=495/519 nm using a nuclear/cytosolic fractionation kit (Cell Biolabs, San Diego, Calif.) according to the manufacturer's protocols. The sum of the averages of the cytoplasm and nucleus of each group was converted to 100% for relative comparison.

Figure 15:
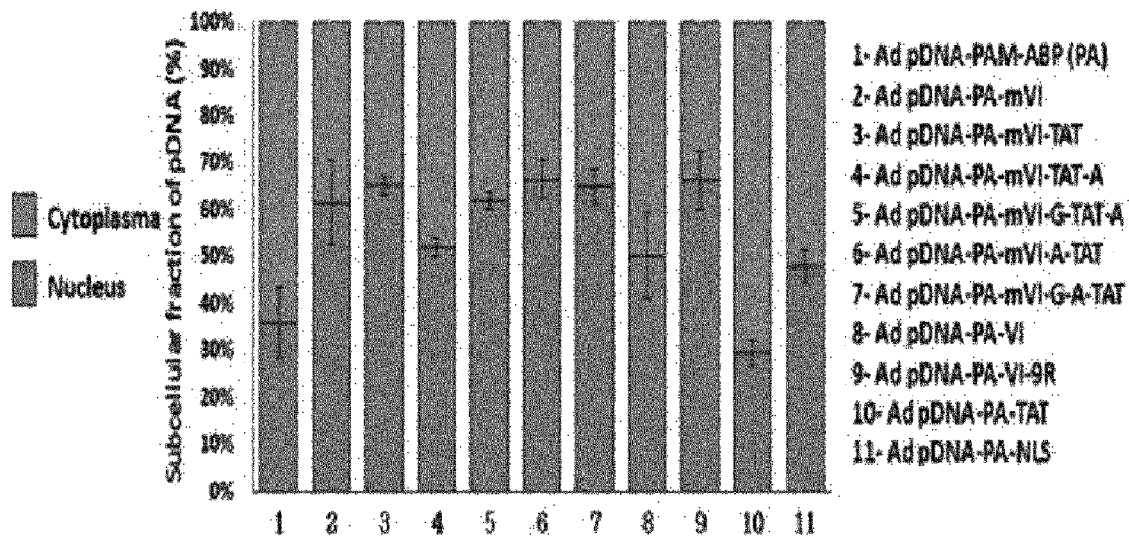
FIG. 15 is a graph for comparing the intracellular localization efficiency of various Ad DNA-polymer-peptide complexes.

As a result of the analysis, compared with when Ad pDNA-PAM-ABP was treated, in all cases of the Ad pDNA-PAM-ABP-peptide complexes, it was confirmed that nuclear localization of Ad pDNA was considerably increased. In addition, compared with the positive control (the Ad pDNA-PAM-ABP-NLS or Ad pDNA-PAM-ABP-TAT complex), the Ad pDNA-PAM-ABP-peptide complexes exhibited an increased nuclear localization ratio (FIG. 15). According to such a result, it was confirmed that, in the case of Ad pDNA-PAM-ABP-peptide complexes, the nuclear localization of Ad DNA was increased by modification of the peptides, resulting in improved adenovirus replication.

Example 12: Confirmation of Virus Proliferation Capability and Oncolytic Capability of Ad pDNA-Polymer-Peptide Complex In this example, to confirm the adenoviral proliferation capability and oncolytic capability of Ad pDNA-polymer-peptide complexes, a complex was manufactured using polymer PAM-ABP and d pDNA containing viral DNA of H-Rd19-k35/DCN/shcMet, which is a tumor-selective oncolytic adenovirus expressing adenovirus DNA such as decorin (DCN) and shcMet. A human uterine cancer cell line, Hela cell line, was inoculated into a 12-well plate, and after 24 hours, treated with naked Ad pDNA, Ad pDNA/PAM-ABP, Ad pDNA/PAM-ABP/peptide complexes in which 6 types of peptides such as mVI, mVI-TAT, mVI-TAT-A, mVI-G-TAT-A, mVI-A-TAT and mVI-G-A-TAT were conjugated with Ad pDNA/PAM-ABP, and controls such as VI-9R and a complex with a TAT peptide. In addition, to verify cytotoxicity, the cells were treated with PAM-ABP or a peptide alone. Four days after the treatment, the culture solution was collected, and the number of adenovirus particles was detected using Q-PCR, and to verify oncolytic capability, 2 mg/ml of 3-(4,5-dimethylthiazol-2-yl)-2,5-diphenyl-tetrazolium bromide (MTT; Sigma Aldrich) in PBS was added at 200 µL to each well of the supernatant-removed plate, and cultured at 37° C. for 4 hours. Afterward, the supernatant was removed, the precipitate was dissolved in 1.0 ml dimethyl sulfoxide, the absorbance was analyzed by reading the plate at 540 nm on a microplate reader, and a non-treated cell group was classified as a negative control.

Figure 16:
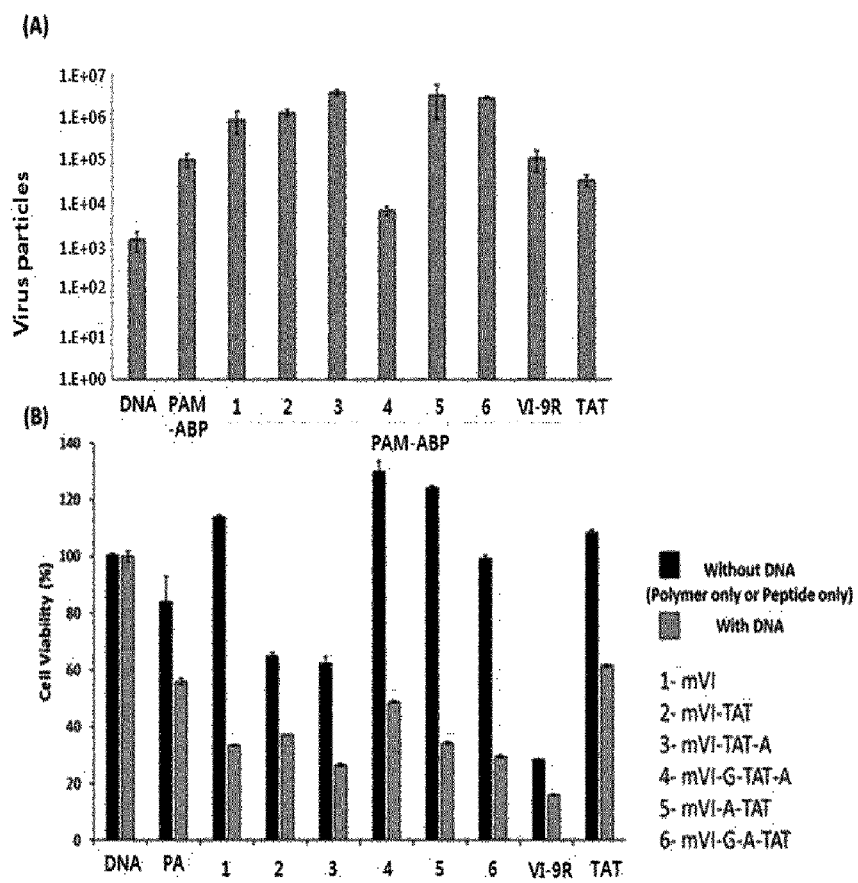

As a result of the analysis, it was confirmed that, when the Hela cell line was treated with only naked Ad pDNA, virus production was $1.5 \times 10^3$ VP, which is a basal level, virus production of the Ad pDNA/PAM-ABP/peptide complexes formed using 6 types of peptides, compared to that of Ad pDNA/PAM-ABP as a control, except the complex using mVI-G-TAT-A, was increased approximately 8.0, 11.6, 34.1, 29.5 and 25.6 times, respectively. Particularly, it was confirmed that, compared with other controls VI-9R or TAT, the virus production of the Ad pDNA/PAM-ABP/peptide complexes was considerably increased (FIG. 16A). In addition, to confirm oncolytic capability and cytotoxicity, when each plate from which a supernatant was removed was treated with an MTT solution, although the VI-9R peptide exhibited high cytotoxicity, the mVI, mVI-G-TAT-A, mVI-A-TAT and mVI-G-A-TAT exhibited relatively high cytotoxicity, and as a result of confirming the oncolytic capability, the Ad pDNA-(PAM-ABP)-peptide complexes formed using the 6 types of peptides exhibited oncolytic capability which was increased 22.5, 18.7, 29.5, 7.1, 21.7, and 26.5%, respectively, compared with the control Ad pDNA/PAM-ABP (FIG. 16B). Particularly, it can be inferred that the highest oncolytic capability of the Ad pDNA/PAM-ABP/peptide complex using VI-9R is caused by the induction of oncolysis by the toxicity of VI-9R itself.

From the result, it can be seen that, in the Ad pDNA-(PAM-ABP)-peptide complexes, viral proliferation in cancer cells was very successful, and adenoviruses proliferated in the tumor cells sequentially led to cancer cell-specific oncolytic capability, and thus viral proliferation capability and oncolytic capability were greatly increased.

Example 13: Verification of Virus Proliferation Capability and Oncolytic Capability of Ad pDNA-Polymer-Peptide Complex In this example, to verify the adenoviral proliferation capability of Ad pDNA-polymer-peptide complexes, a complex was manufactured using polymer PAM-ABP and Ad pDNA including viral DNA of green fluorescent protein (GFP)-expressing tumor-selective adenovirus RdB/GFP as adenovirus DNA. A human lung cancer cell line such as an A549 cell line was inoculated into a 12-well plate, and after 24 hours, treated with naked Ad pDNA, Ad pDNA/PAM-ABP, Ad pDNA/PAM-ABP/peptide complexes in which 6 types of peptides such as mVI, mVI-TAT, mVI-TAT-A, mVI-G-TAT-A, mVI-A-TAT and mVI-G-A-TAT were conjugated with Ad pDNA-(PAM-ABP), and controls such as VI-9R and a complex with TAT peptide. Four days after the treatment, the culture solution was collected, and the number of adenovirus particles was confirmed using Q-PCR.

Figure 17:
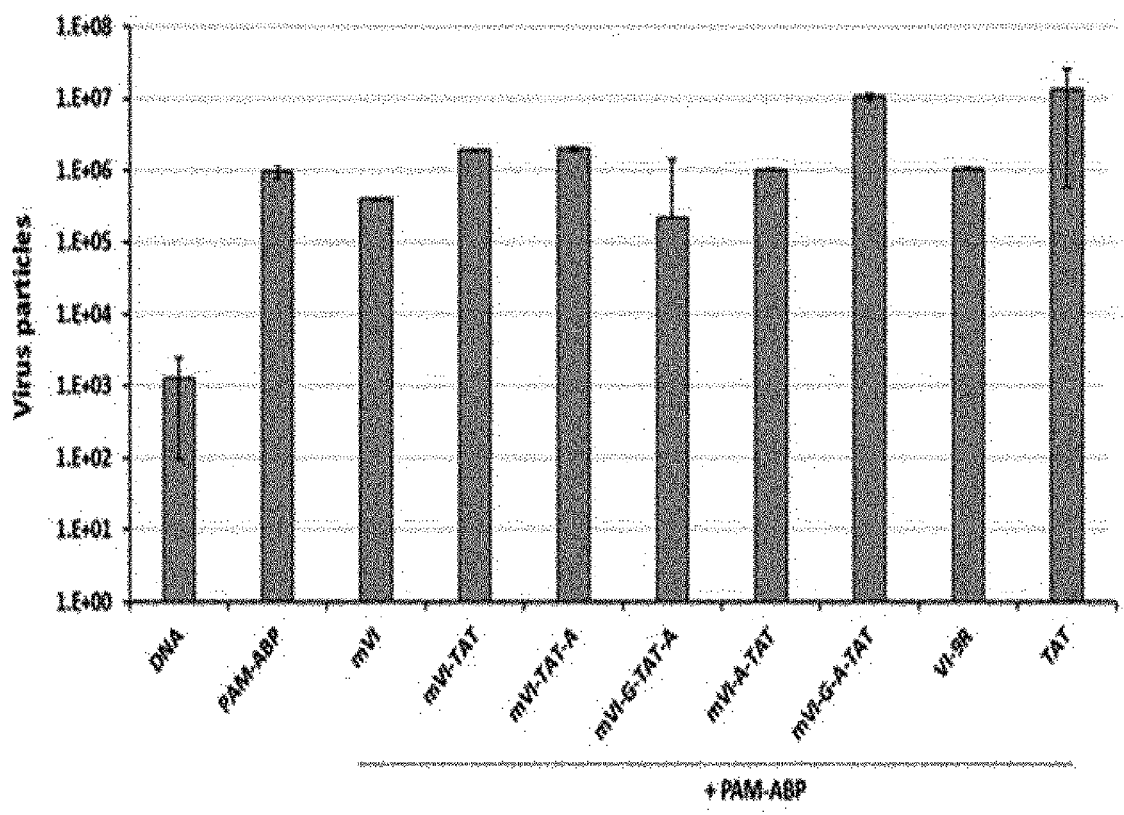
FIG. 17 represents the result that confirms viral proliferation capability of an Ad DNA-polymer-peptide complex (Ad pDNA-(PAM-ABP)-peptide) by measuring the number of virus particles through Q-PCR.

As a result of the analysis, it was confirmed that, when the A549 cell line was treated with only naked Ad pDNA, virus production was $1.2 \times 10^3$ VP, which was a basal level, and virus production of the Ad pDNA-(PAM-ABP)-peptide complexes formed using the 6 types of peptides, compared with the control Ad pDNA/PAM-ABP, except the complexes using mVI and mVI-G-TAT-A, was increased approximately 1.95, 2.01, 1.03 and 10.7 times, and particularly, the virus production of the Ad pDNA-(PAM-ABP)-peptide complexes was also considerably increased, compared with a different control VI-9R or TAT (FIG. 17).

Example 14: Confirmation of Intracellular Gene Delivery Efficiency Increased by Ad pDNA-Polymer-Dimer Peptide Complex In this example, to confirm the intracellular gene delivery efficiency of Ad pDNA(dE1/GFP)-(PAM-ABP)-dimeric peptide complexes, a 293A cell line was inoculated into a 24-well plate, grown to 60 to 70% confluence, and treated with a modified monomer peptide, a dimeric peptide and the Ad pDNA-(PAM-ABP)-dimeric peptide complexes, and 48 hours after the treatment, GFP expression was observed using fluorescence microscopy.

Meanwhile, the dimeric peptide was manufactured using an air oxidation technique. Specifically, 2 mg of a monomer peptide was dissolved in 2 mL of 0.1 M deaerated ammonium bicarbonate, and the mixture was stirred for 24 hours at room temperature while a cap was open. Afterward, the monomer peptide was separated using a dialysis cassette, the remaining reactant was subjected to freeze-drying, thereby obtaining a powder. As controls, TAT, a complex formed using a pre-modified peptide (mVI-G-A-TAT), PEI25k, and a complex in which PAM-ABP polymer was conjugated with Ad pDNA were used.

In addition, the intracellular gene delivery efficiency of an Ad pDNA(RdB/GFP)-(PPCBA-PEI-Arg)-peptide complex using a different polymer PPCBA-PEI-Arg was confirmed, to this end, an 293A cell line was inoculated into a 24-well plate and grown to 60 to 70% confluence, and after 24 hours, Ad pDNA-(PPCBA-PEI-Arg)-dimeric peptide was prepared by being bound with a modified dimeric peptide at a ratio of 1:20 or 1:30 (Ad pDNA:PPCBA-PEI-Arg weight ratio) and then used to treat the cells. Four days after the treatment, GFP expression was observed using fluorescence microscopy. As controls, Ad pDNA/PEI25K and Ad pDNA/Lipofectamine were used.

Figure 18:
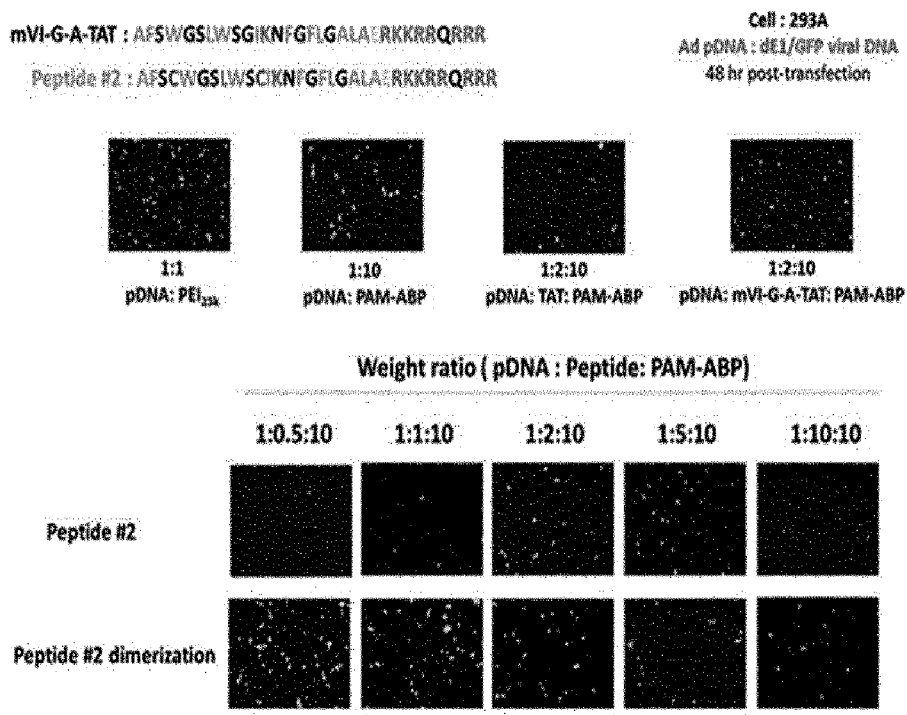
FIG. 18 represents the result that confirms the intracellular gene delivery efficiency of an Ad DNA-polymer-dimer peptide complex (Ad pDNA-(PAM-ABP)-peptide).

As a result of the analysis, when the Ad pDNA-polymer-dimeric peptide complex was treated, compared with when Ad pDNA-PEI$_{25k}$, or Ad pDNA-PAM-ABP was treated, GFP expression was considerably increased. In addition, it was confirmed that, when the mVI-G-A-TAT peptide was modified, GFP expression was similar to that of an unmodified peptide, but when a modified monomer peptide was changed to a dimeric peptide, and then the Ad pDNA-polymer-peptide complex was treated, compared to the control, GFP expression was considerably increased (FIG. 18).

Figure 19:
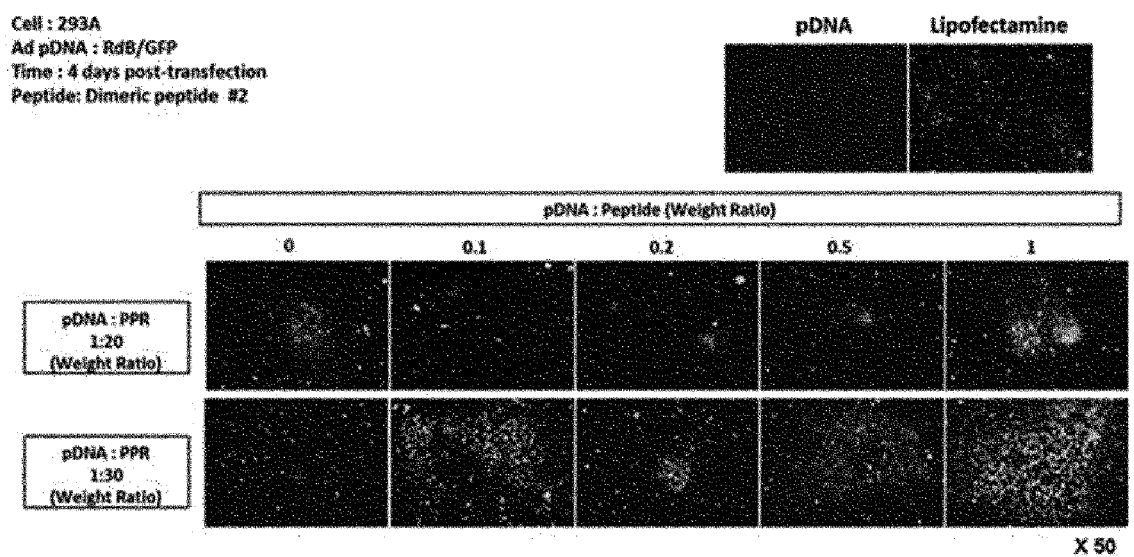
FIG. 19 represents the result that confirms the intracellular gene delivery efficiency of an Ad DNA-polymer-dimer peptide complex (Ad pDNA-(PPCBA-PEI-Arg)-peptide).

In addition, it was confirmed that, when the treated Ad pDNA-(PPCBA-PEI-Arg)-dimeric peptide complex consists of Ad pDNA, a polymer and a peptide at a weight ratio of 1:30:1, compared with when the control such as Ad pDNA-PEI25K or Ad pDNA-lipofectamine was treated, GFP expression was considerably increased, and generally, when the weight ratio of Ad pDNA:Polymer was 30:1, compared with when the weight ratio was 20:1, the effect caused thereby was excellent, and as an amount of the dimeric peptides that are bound was increased, GFP expression was concentration-dependently increased (FIG. 19). That is, from the result, it was seen that intracellular delivery efficiency may be further improved by modifying the peptide of the present invention in a dimeric form.

Example 15: Confirmation of Virus Proliferation Capability and Oncolytic Capability of Ad pDNA-Polymer-Dimer Peptide Complex In this example, to confirm the adenoviral proliferation capability of Ad pDNA-polymer-dimeric peptide complexes, a complex was manufactured using polymer PPCBA-PEI-Arg(PPR) and Ad pDNA containing viral DNA of a tumor-selective oncolytic adenovirus, RdB/IL-12/GMCSF, expressing IL-12 and GMCSF as adenovirus DNA. A human prostate cancer cell line, that is, a PC-3 cell line, was inoculated into a 12-well plate, and after 24 hours, treated with each of complexes prepared using naked Ad pDNA, PPCBA-PEI-Arg(PPR), a dimeric peptide, Ad pDNA-Lipofectamine, Ad pDNA-PPR, Ad pDNA-PPR-dimeric peptide (1:30:0.01, 1:30:0.05 [Ad pDNA:polymer: peptide weight ratio]). Four days after the treatment, the culture solution was collected, and the number of adenovirus particles was identified using Q-PCR. In addition, a hamster pancreatic cancer cell line, that is, a HapT1 cell line, was inoculated into a 12-well plate, and after 24 hours, treated with each of complexes prepared using naked Ad pDNA, PPCBA-PEI-Arg(PPR), a dimeric peptide, Ad pDNA-Lipofectamine, Ad pDNA-PPR, Ad pDNA-PPR-dimeric peptide (1:30:0.01, 1:30:0.05 [Ad pDNA:polymer:peptide weight ratio]). Four days after the treatment, the culture solution was collected, and the number of adenovirus particles was identified using Q-PCR.

Moreover, to verify oncolytic capability, 200 μL of 2 mg/ml 3-(4,5-dimethylthiazol-2-yl)-2,5-diphenyl-tetrazolium bromide (MTT; Sigma Aldrich) in PBS was added to each well of a plate from which a supernatant was removed, and cultured at 37° C. for 4 hours. Afterward, the supernatant was removed, a precipitate was dissolved in 1.0 ml of dimethyl sulfoxide, the absorbance of the plate was read at 540 nm on a microplate reader. Non-treated cell groups were classified as negative controls.

Figure 20:
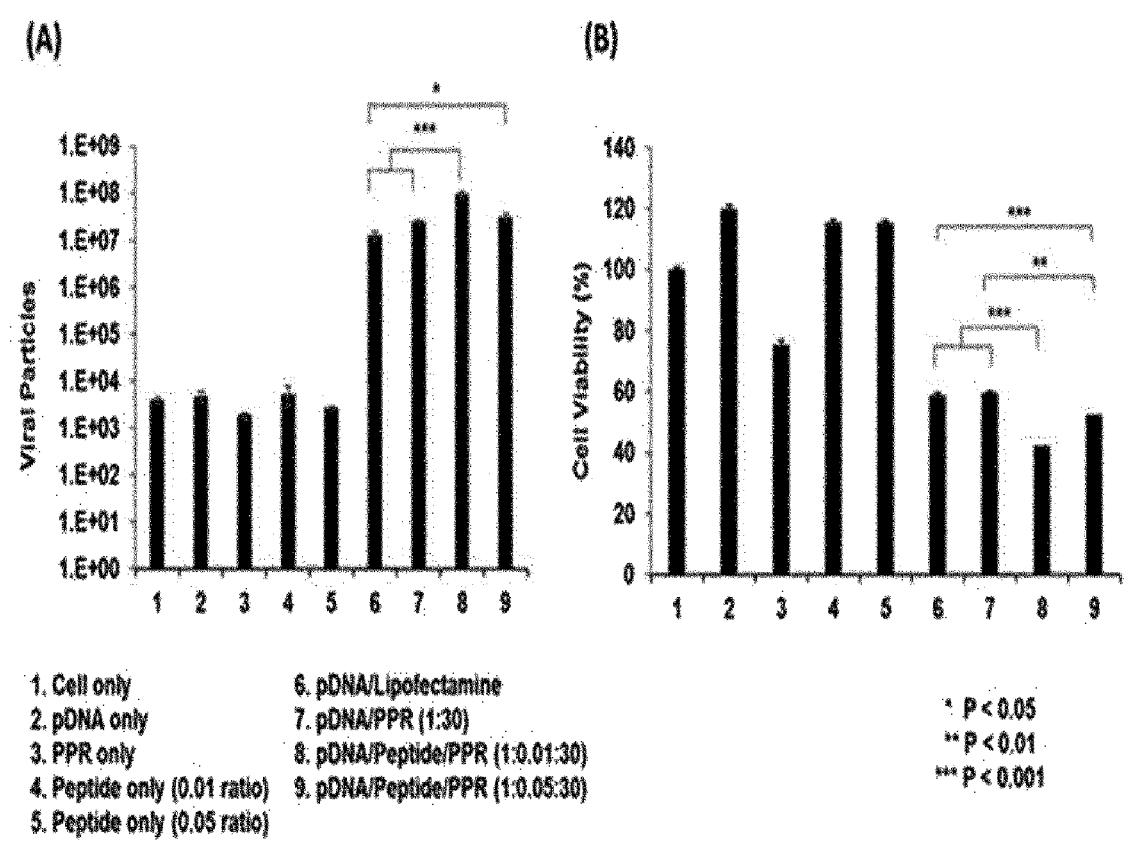
Figure 21:
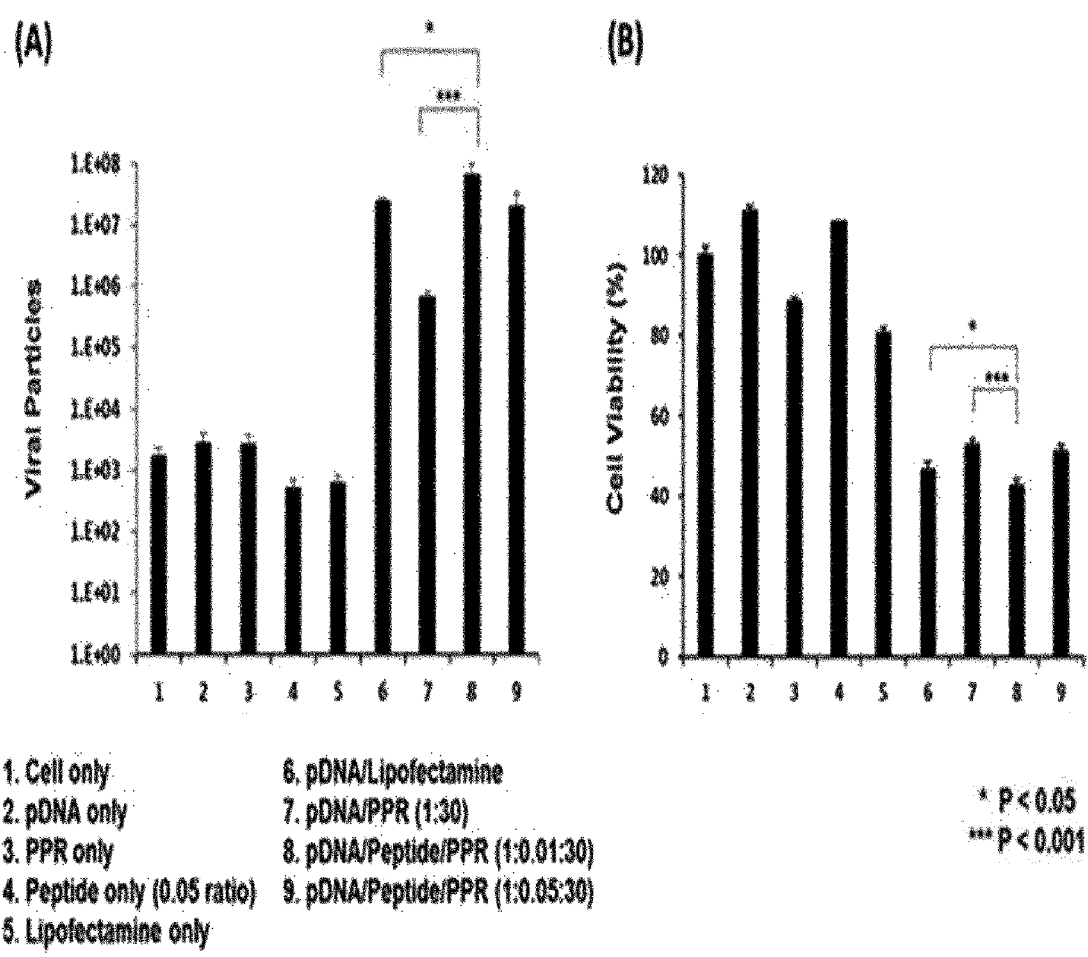
Figure 22:
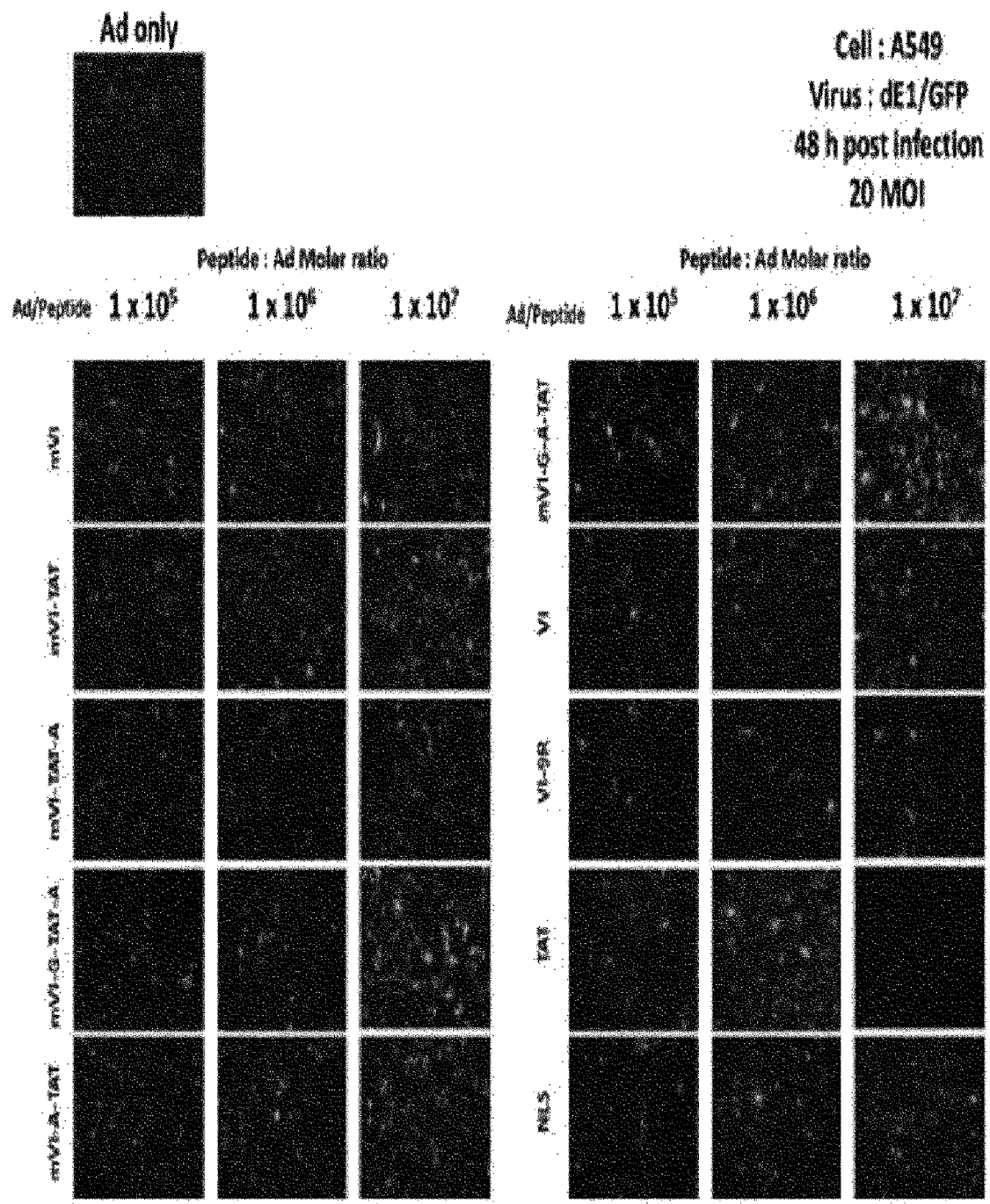
FIG. 22 represents the results that confirm the intracellular gene delivery efficiency of adenovirus/peptide complexes (Ad/peptide complexes) in an A549 cell line.
Figure 23:
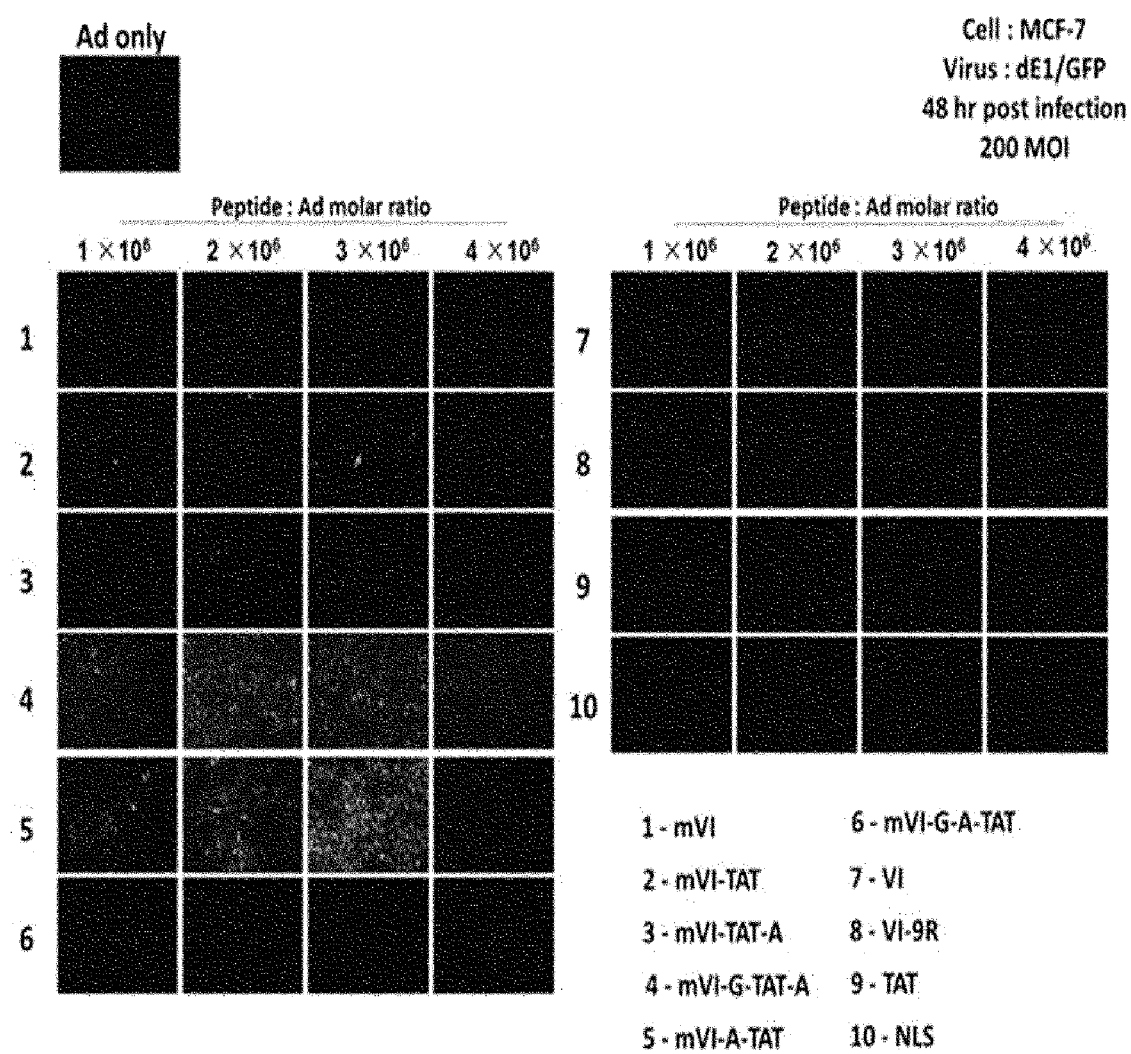
FIG. 23 represents the results that confirm the intracellular gene delivery efficiency of adenovirus/peptide complexes (Ad/peptide complexes) in an MCF-7 cell line.
Figure 24:
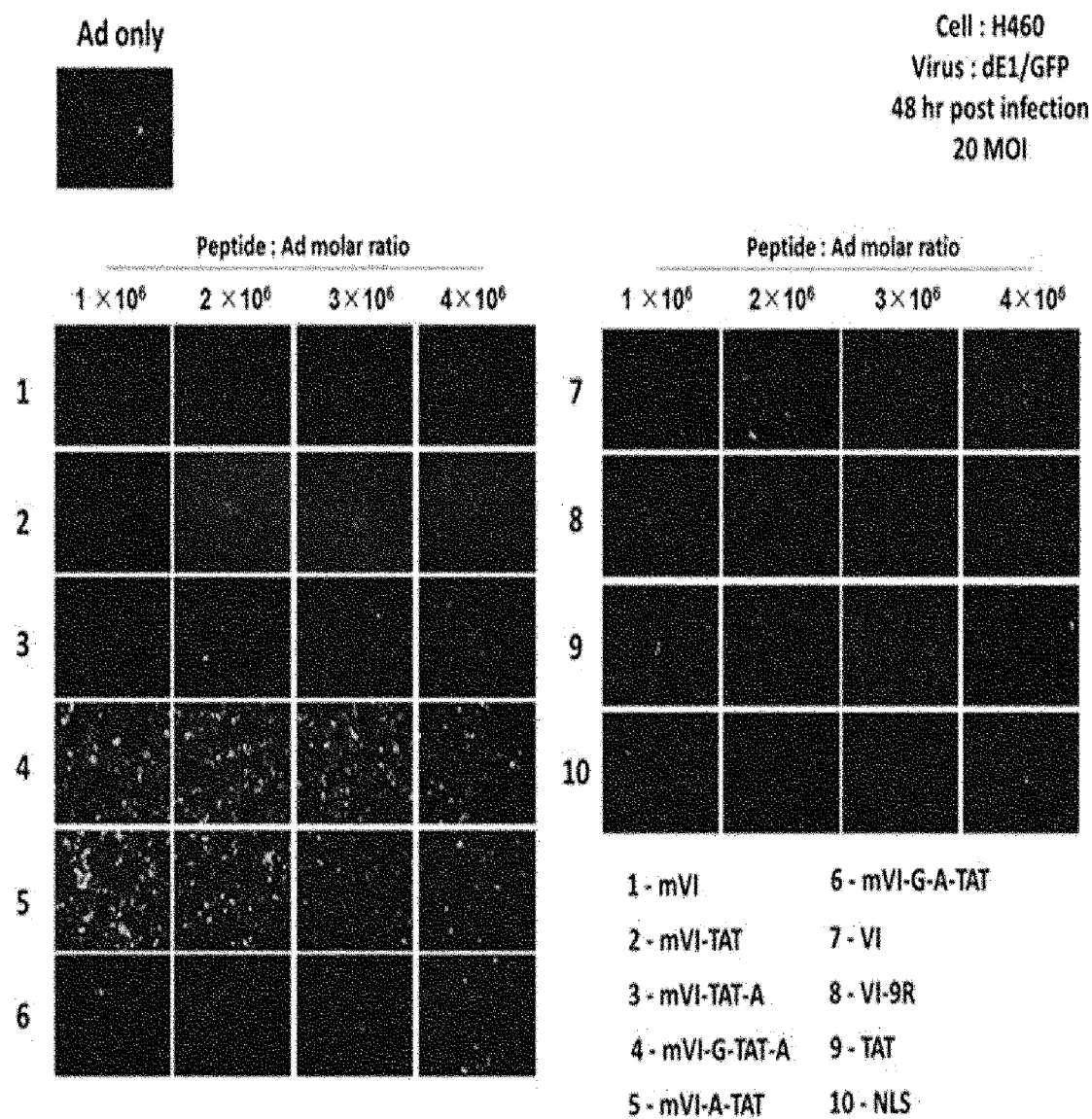
FIG. 24 represents the results that confirm the intracellular gene delivery efficiency of adenovirus/peptide complexes (Ad/peptide complexes) in an H460 cell line.
Figure 25:
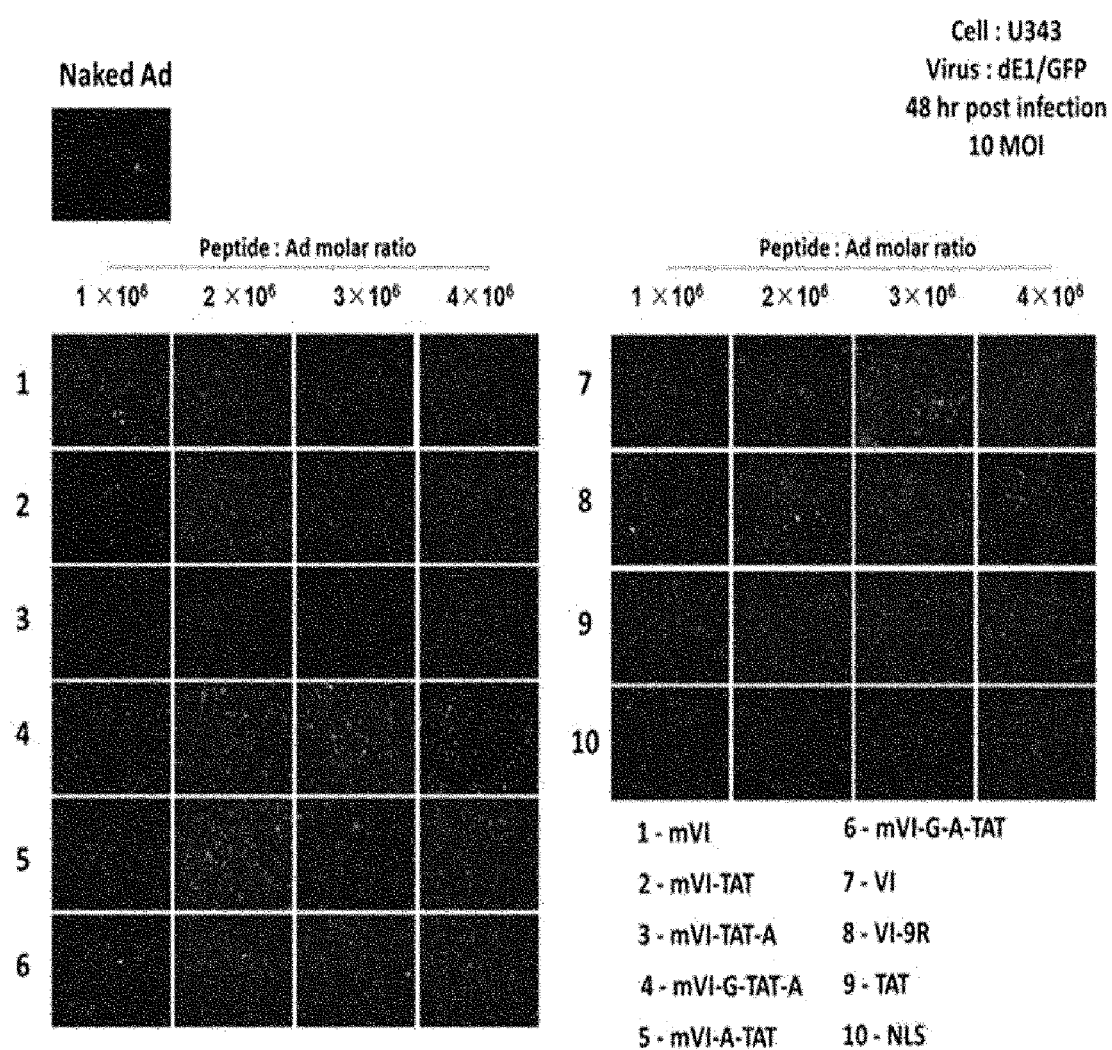
FIG. 25 represents the results that confirm the intracellular gene delivery efficiency of adenovirus/peptide complexes (Ad/peptide complexes) in an U343 cell line.

As a result of the analysis, when the PC-3 cell line was treated with only naked Ad pDNA, virus production was $4.6 \times 10^3$ VP, which was a basal level. It can be confirmed that, when the weight ratio of a peptide and Ad pDNA in the group treated with the Ad pDNA-PPR-dimeric peptide complex was 1:0.01, virus production was at the highest level ($9.3 \times 10^7$ VP), which was 7.3 times higher than that of the cell line treated with the control, Ad pDNA-PPR ($2.4 \times 10^6$ VP), and also 3.7 times higher than that of the cell line treated with the positive control, the Ad pDNA-Lipofectamine complex ($2.5 \times 10^7$ VP) (FIG. 20A). In addition, when the HapT1 cell line was treated with only naked Ad pDNA, virus production was $4.6 \times 10^3$ VP, which was a basal level. Like the above-mentioned result, it can be confirmed that, when the weight ratio of a peptide and Ad pDNA in the group treated with the Ad pDNA-PPR-dimeric peptide complex was 1:0.01, virus production was at the highest level ($6.5 \times 10^7$ VP), which was 99.4 times higher than the cell line treated with the control, Ad pDNA/PPR ($6.5 \times 10^5$ VP), and also 2.6 times higher than the cell line treated with a positive control, the Ad pDNA/Lipofectamine complex ($2.4 \times 10^7$ VP) (FIG. 21A)

In addition, as a result of an MTT assay to verify oncolytic capability, in the PC-3 cell line, when the weight ratio of a peptide and Ad pDNA in the group treated with the Ad pDNA-PPR-dimeric peptide complex was 1:0.01, the oncolytic capability was at the highest level of 57.6%, which was caused by 17.1% and 16.2% increases in oncolytic effect, compared with the group treated with the Ad pDNA-Lipofectamine complex or the Ad pDNA-PPR group as controls, respectively (FIG. 20B). In addition, even in the HapT-1 cell line, when the weight ratio of a peptide and Ad pDNA in the group treated with the Ad pDNA-PPR-dimeric peptide complex was 1:0.01, the oncolytic capability was at the highest level of 57.3%, which was caused by 4% and 10.5% increases in oncolytic effects, compared with the group treated with the Ad pDNA-Lipofectamine complex or the Ad pDNA-PPR group, respectively (FIG. 21B).

From the result, it can be seen that, when the weight ratio of a peptide and Ad pDNA in the group treated with Ad pDN-/PPR-dimeric peptide was 1:0.01, the highest adenoviral proliferation capability and the highest oncolytic capability were exhibited. Such a result shows that the Ad pDNA-PPR-dimeric peptide complex exhibited very successful viral proliferation in cancer cells, the adenoviruses proliferated in tumor cells sequentially exhibited cancer cell-specific oncolytic capability, and therefore the virus proliferation capability and the oncolytic capability were greatly increased.

Example 16: Confirmation of Intracellular Gene Delivery Efficiency of Adenovirus/Peptide Complex In this example, to confirm the intracellular delivery efficiency of an adenovirus (dE1/GFP)-peptide complex, various cell lines (A549, MCF, H460, and U434) were inoculated into 24-well plates and grown to 60 to 70% confluence, and after 24 hours, 8 types of peptides such as VI, VI-9R, mVI, mVI-TAT, mVI-TAT-A, mVI-G-TAT-A, mVI-A-TAT and mVI-G-A-TAT were conjugated with adenoviruses (dE1/GFP) at $1:1\times10^5$, $1:1\times10^6$ and $1:1\times10^7$ molar ratios, and then used at 20 MOI to treat the cells. After 48 hours of the treatment, GFP expression was observed using fluorescence microscopy. An adenovirus that was conjugated with neither NLS, TAT nor a peptide (adenovirus only) was used as a control for an experiment using the A549 cell line, and an adenovirus only group that was conjugated with neither VI, VI-9R, NLS, TAT nor a peptide was used as a control for other cell lines.

The adenovirus (dE1/GFP)/peptide complexes were transfected into the cells, and then gene delivery efficiencies were compared. Compared with the adenovirus only group, the gene delivery efficiencies of the Ad/peptide complexes were generally higher (FIGS. 22 to 25). Particularly, it can be confirmed that, when the 6 types of modified peptides such as mVI, mVI-TAT, mVI-TAT-A, mVI-G-TAT-A, mVI-A-TAT and mVI-G-A-TAT were conjugated with Ad, the gene delivery efficiencies of the Ad/peptide complexes were considerably increased, compared with the Ad/VI and Ad/VI-9R groups.

Therefore, it was seen that the peptide of the present invention can increase the intracellular delivery efficiency of a nucleic acid such as adenovirus DNA, and also improve the intracellular delivery efficiency of a virus itself, and such a trend can be enhanced by peptide modification.

Example 17: Confirmation of Cellular Uptake Efficiency Increased by Chemotherapeutic/Peptide Complex In this example, to confirm the cellular uptake increased by a chemotherapeutic/peptide complex, a U343 or H460 cell line was inoculated into a 12-well plate and grown to 70 to 80% confluence. Specifically, in the case of physical bonding (DOX+mVI-G-A-Tat), a chemotherapeutic, that is, doxorubicin and a mVI-G-A-TAT peptide were put into a tube containing PBS buffer, stored at room temperature for 20 minutes and reacted under physiological conditions, and then 5 μM of the cells were treated with the complex. In addition, in the case of chemical bonding (mVI-G-A-Tat conjugated DOX), DOX (820 μg) and N-β-maleimidopropionic acid hydrazide (BMPH) as a crosslinking agent (1.1 equiv) were added to 800 μL of DMSO buffer and mixed. The corresponding reaction was carried out at room temperature for 24 hours in a dark condition, and then, a peptide (4 mg) was added to make the ratio of the DOX:mVI-G-A-Tat peptide 1.1 equiv, and reacted at room temperature for 3 hours. Finally, an unreacted chemotherapeutic was removed using a 3.5 kDa dialysis cassette, lyophilized to form a powder and dissolved in PBS, and then the cells were treated with 5 μM of the complex. At 5, 10, and 30, and 120 minutes after the treatment, cellular doxorubicin uptake was quantified by FACS, and a group treated with only a chemotherapeutic was used as a control.

Figure 26:
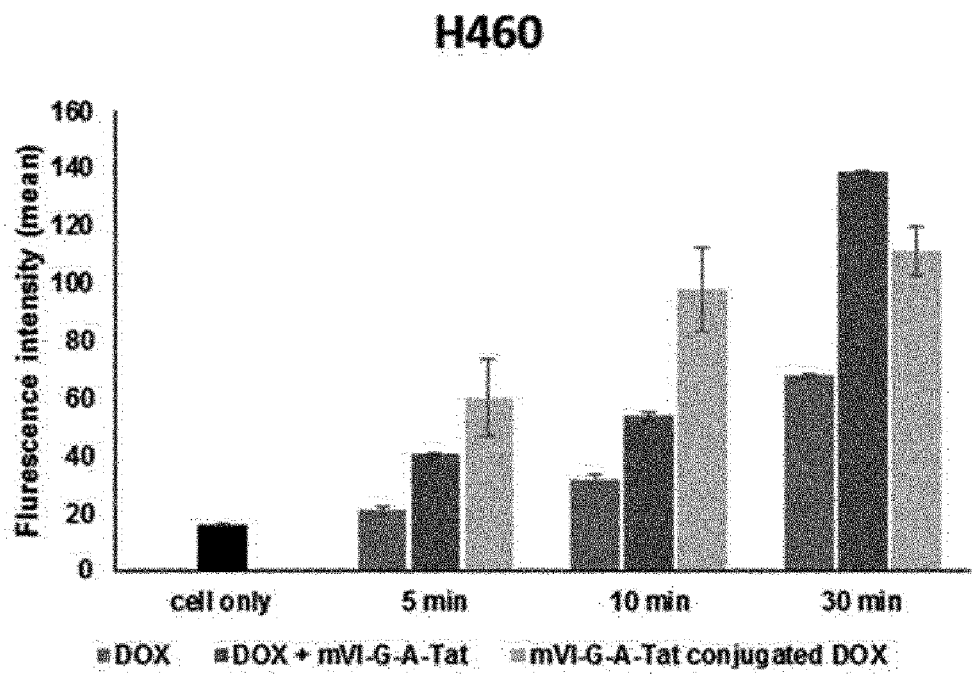
FIG. 26 represents the results of comparative analysis of the cell absorption efficiency of chemotherapeutic/peptide complexes.

As a result of treatment of the cells with the chemotherapeutic/peptide complex and confirmation of cellular uptake, compared with the control that treated with only a chemotherapeutic, the cellular uptake of the chemotherapeutic/peptide complex was increased, and particularly, it can be confirmed that, when a chemotherapeutic was physically bound with a peptide, efficiency of cellular drug uptake at an initial time is greatly increased (FIG. 26).

Therefore, it can be seen that the amount of the cellular chemotherapeutic uptake was increased by intracellularly delivering a modified Ad protein VI-derived peptide together with a chemotherapeutic, resulting in further improvement of a therapeutic effect.

Example 18: Confirmation of Oncolytic Effect Increased by Chemotherapeutic/Peptide Complex In this example, to confirm the oncolytic effect increased by a chemotherapeutic/peptide complex, an H460, A549 or U343 cell line was inoculated into a 96-well plate and grown to 60 to 70% confluence, and after 24 hours, a chemotherapeutic such as MG132 or doxorubicin was bound with mVI-G-A-TAT peptide physically (mVI-G-A-Tat+MG132, DOX+mVI-G-A-Tat) or chemically (mVI-G-A-Tat conjugated MG123/DOX), and then treated at 0.1 to 5 μM. 48 hours after the treatment, cell viability was confirmed by performing an MTT assay, and a group treated with only either of mVI-G-A-TAT peptide, MG132, or doxorubicin was used as a control.

Figure 27:
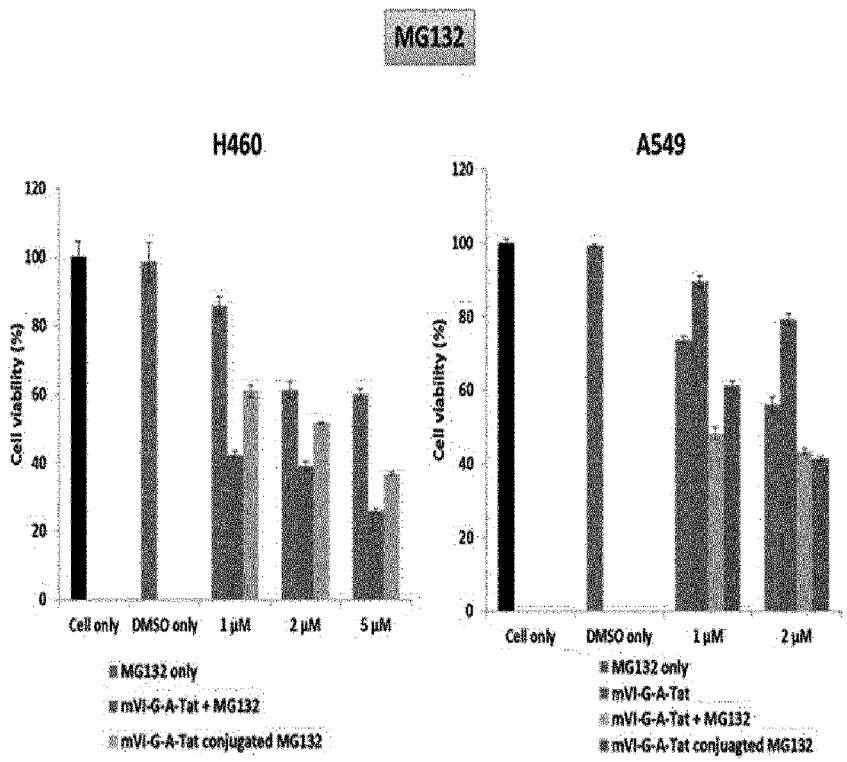
FIG. 27 represents the results that confirm the oncolytic capability of chemotherapeutic/peptide complexes (MG123/peptide complexes).
Figure 28:
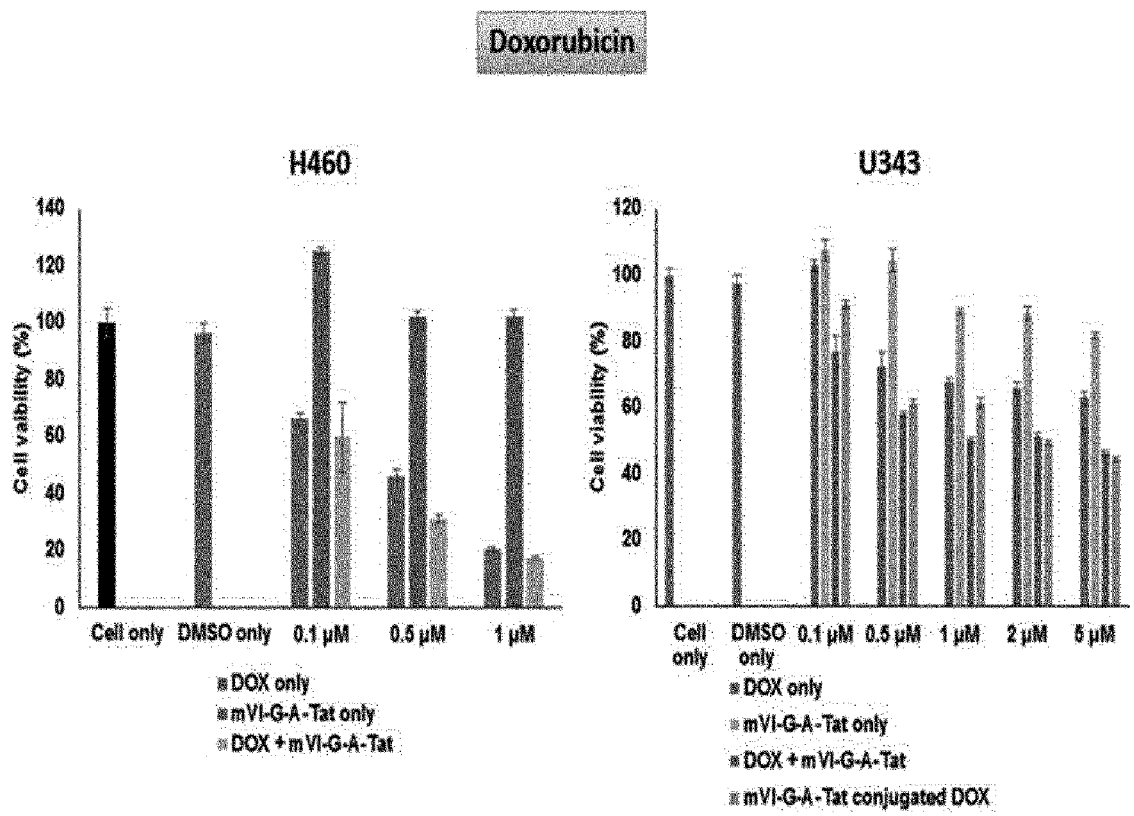
FIG. 28 shows the oncolytic capability of chemotherapeutic/peptide complexes (DOX/peptide complexes).

As a result of confirming the treating of the cells with the chemotherapeutic/peptide complex and confirming the oncolytic effect, compared with the control group treated only with a chemotherapeutic, it can be confirmed that the oncolytic effect of the chemotherapeutic/peptide complex was increased, and particularly, when a chemotherapeutic was physically bound with a peptide, compared with chemical binding, it can be confirmed that its effect was further increased (FIGS. 27 and 28).

Therefore, it can be seen that the oncolytic capability caused by the chemotherapeutic was increased by intracellularly delivering a modified Ad protein VI-derived peptide together with a chemotherapeutic.

Example 19: Confirmation of Delivery Efficiency into Cancer Cells, Increased by Protein/Peptide Complex In this example, to confirm the intracellular delivery efficiency of a protein (Human serum albumin)/peptide complex, a lung cancer cell line, that is, an A549 cell line, was inoculated into a 96-well plate and grown to 70 to 80% confluence, and after 24 hours, FITC-labeled human serum albumin (HSA) and mVI-G-A-TAT peptide were physically bound, and then treated at 0.5 or 5 µM (refer to the physical binding process described in Example 17). 0.16, 0.5, 2 or 6 hours after the treatment, intracellular FITC-labeled HSA uptake was confirmed using a microplate reader, and a group treated with only the protein was used as a control.

As a result of treating the cells with the protein (HSA)/peptide complex and confirming the cellular uptake of the complex, compared with the control only treated with the protein, it can be confirmed that the cellular uptake of the protein/peptide complex was increased, and particularly, in all experimental groups treated with 0.5 or 5 µM of the protein, when also treated with the peptide of the present invention, compared with the group only treated with the protein, a statistically significant increase in intracellular protein delivery efficiency was exhibited (FIG. 29). Therefore, it can be seen that the intracellular delivery efficiency of the protein was further increased by intracellularly delivering a modified Ad protein VI-derived peptide and a protein.

Example 20: Confirmation of Intracellular Antibody Delivery Efficiency Increased by Antibody/Peptide Complex In this example, it was intended to identify the intracellular delivery efficiency of an antibody (rabbit polyclonal to TGF beta 1)/peptide complex. A transforming growth factor beta (TGF-β) is a protein present in the cytoplasm, has been known to be overexpressed in cancer cells, and requires high permeability with respect to the cell membrane for an antigen-antibody reaction induced by an antibody administered from an outside. In this example, to confirm whether a modified Ad protein VI-derived peptide can deliver an antibody into cells, the cells were treated with the antibody (rabbit polyclonal to TGF beta 1)/peptide complex without permeabilization, whether the intracellular delivery occurred was confirmed. Specifically, a lung cancer cell line, that is, an A549 cell line, was inoculated on a chamber slide and grown to 70 to 80% confluence, and after 24 hours, an antibody was physically bound to a mVI-G-A-TAT peptide at a weight ratio of 1:1 (refer to the physical binding process described in Example 17), and then treated at 4 µg. For 2 hours, after the treatment, cellular antibody uptake was observed by fluorescent microscopy using an Alexa Fluor 488 conjugated antibody (Alexa Fluor 488 goat anti-rabbit IgG (H+L)), and a group only treated with the antibody was used as a control.

As a result of the analysis, in the control only treated with the antibody, it can be confirmed that most antibodies were not delivered into the cells, but a great quantity of antibodies was delivered into the cells in the group treated with the antibody/peptide complex (FIG. 30). Through this, it can be seen that the intracellular delivery efficiency of the antibody is further increased by intracellularly delivering a modified Ad protein VI-derived peptide and an antibody.

Above, specific parts of the present invention have been described in detail. It is apparent to those of ordinary skill in the art that such specific descriptions are merely specific embodiments, and the scope of the present invention is not limited thereto. Therefore, the substantial scope of the present invention is to be defined by the accompanying claims and equivalents thereof.

---

The invention claimed is:

1. A method for cellular delivery of a bioactive substance, comprising:
   treating cells with a complex of a peptide and a bioactive substance,
   wherein the peptide consists of an amino acid sequence selected from the group consisting of SEQ ID NO: 4, SEQ ID NO:5, SEQ ID NO: 6, SEQ ID NO: 7, SEQ ID NO; 8 and SEQ ID NO: 11, and
   wherein the bioactive substance is any one selected from the group consisting of a nucleic acid, a peptide, a polypeptide, an antibody, a chemotherapeutic and a virus.

2. A method for treating cancer, comprising:
   administering a composition comprising (a) a therapeutically effective amount of a complex of a tumor-selective oncolytic adenovirus or a viral DNA and a peptide and (b) a pharmaceutically acceptable carrier into a subject,
   wherein the peptide consists of an amino acid sequence selected from the group consisting of SEQ ID NO: 4, SEQ ID NO:5, SEQ ID NO: 6, SEQ ID NO: 7, SEQ ID NO; 8 and SEQ ID NO: 11.

3. The method of claim 1, wherein the peptide is a dimer of the peptide consisting of an amino acid sequence of SEQ ID NO: 4, SEQ ID NO: 5, SEQ ID NO: 6, SEQ ID NO: 7 or SEQ ID NO: 8.

4. The method of claim 1, wherein the complex further comprises a biocompatible polymer.

5. The method of claim 2, wherein the peptide is a dimer of the peptide consisting of an amino acid sequence of SEQ ID NO: 4, SEQ ID NO: 5, SEQ ID NO: 6, SEQ ID NO: 7 or SEQ ID NO: 8.

6. The method of claim 5, wherein the complex further comprises a biocompatible polymer.

7. The method of claim 5, wherein the cancer is breast cancer, lung cancer, stomach cancer, liver cancer, blood cancer, bone cancer, pancreatic cancer, skin cancer, head and neck cancer, ovarian cancer, rectal cancer, anal cancer, colorectal cancer, tubal cancer, endometrial cancer, uterine cervical cancer, small bowel neoplasm, endocrine carcinoma, bladder cancer, larynx cancer, osteosarcoma, thyroid cancer, brain cancer, colon cancer, vaginal cancer, vulvar cancer, esophageal cancer, adrenal gland cancer, lymphoma, ureteral cancer, central nervous system (CNS) tumor, a spinal cord tumor, nasopharyngeal cancer, parathyroid cancer, kidney cancer, soft tissue sarcoma, a urethral tumor, prostate cancer, bronchial cancer or bone marrow cancer.

8. The method of claim 5, wherein the cancer is selected from the group consisting of dermal melanoma, ocular melanoma, uterine sarcoma, Hodgkin's disease, penile carcinoma, acute leukemia, renal pelvic carcinoma, brain stem glioma and pituitary adenoma.

9. A composition for intracellular delivery of bioactive substance, comprising: a complex of a peptide and a bioactive substance,
   wherein the peptide consists of an amino acid sequence selected from the group consisting of SEQ ID NO: 4, SEQ ID NO:5, SEQ ID NO: 6, SEQ ID NO: 7, SEQ ID NO; 8 and SEQ ID NO: 11, and
   wherein the bioactive substance is any one selected from the group consisting of a nucleic acid, a peptide, a polypeptide, an antibody, a chemotherapeutic and a virus.

* * * * *